US008630867B2

(12) United States Patent
Yoo

(10) Patent No.: US 8,630,867 B2
(45) Date of Patent: Jan. 14, 2014

(54) REMOTE-MEDICAL-DIAGNOSIS SYSTEM METHOD

(75) Inventor: Jae-chern Yoo, Gwacheon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 797 days.

(21) Appl. No.: 12/596,373

(22) PCT Filed: Apr. 22, 2008

(86) PCT No.: PCT/KR2008/002262
§ 371 (c)(1),
(2), (4) Date: Oct. 16, 2009

(87) PCT Pub. No.: WO2008/130178
PCT Pub. Date: Oct. 30, 2008

(65) Prior Publication Data
US 2010/0121156 A1 May 13, 2010

(30) Foreign Application Priority Data
Apr. 23, 2007 (KR) .................. 10-2007-0040657

(51) Int. Cl.
*G06Q 10/00* (2012.01)
*G06Q 50/00* (2012.01)

(52) U.S. Cl.
USPC .................................. 705/2; 705/3

(58) Field of Classification Search
USPC ............................................ 705/2, 3
See application file for complete search history.

(56) References Cited

U.S. PATENT DOCUMENTS

| 4,712,562 | A | 12/1987 | Ohayon et al. |
| 4,764,870 | A | 8/1988 | Haskin |
| 4,889,132 | A | 12/1989 | Hutcheson et al. |
| 2002/0065682 | A1* | 5/2002 | Goldenberg .................. 705/2 |
| 2002/0111741 | A1* | 8/2002 | Abraham-Fuchs et al. .... 702/19 |
| 2002/0118355 | A1* | 8/2002 | Worthington et al. ......... 356/72 |

(Continued)

FOREIGN PATENT DOCUMENTS

| CA | 1 153 441 | 9/1983 |
| JP | 52-020050 | 2/1977 |

(Continued)

*Primary Examiner* — Neha Patel
(74) *Attorney, Agent, or Firm* — Staas & Halsey LLP

(57) ABSTRACT

Provided are a remote medical-diagnosis system including: a bio-disc or a biochip performing biological, chemical or biochemical reactions with a sample, and having a barcode or a RF IC; a bioanalytical device analyzing results of reactions performed by the bio-disc or the biochip and including a reader reading the barcode or the RF IC to authenticate the bio-disc or the biochip or recording the measured data to the RF IC regardless of a connection with a remote diagnosis server; a virtual doctor as a software in a user's terminal, the virtual doctor providing a user with guidelines and instructions as how to use the bioanalytical device, and providing the user with a consulting service, a diagnosis unit self-analyzing the measured data using mathematical calculations and outputting results of a diagnosis; a user's terminal providing the user with a consulting service from a medical expert or a virtual doctor; a medical expert's terminal providing the user with a consulting service; and a remote diagnosis server connecting the user with the medical expert during periodic medical consultations, connecting the user with the virtual doctor during non-periodic medical consultations, blocking connection between the user and the virtual doctor if a periodic medical consultations term has elapsed; and a method of performing the remote medical-diagnosis.

22 Claims, 13 Drawing Sheets

(56) References Cited

U.S. PATENT DOCUMENTS

| | | |
|---|---|---|
| 2006/0035247 A1* | 2/2006 | Ko et al. ............... 435/6 |
| 2006/0161457 A1* | 7/2006 | Rapaport et al. ............ 705/2 |
| 2008/0077028 A1* | 3/2008 | Schaldach et al. ............ 600/509 |

FOREIGN PATENT DOCUMENTS

| | | |
|---|---|---|
| JP | 54-114008 | 9/1979 |
| JP | 57-008418 | 1/1982 |
| JP | 59-047872 | 3/1984 |
| JP | 63-021870 | 1/1988 |
| JP | 02-218336 | 8/1990 |
| JP | 11-206722 | 8/1999 |
| JP | 3623500 | 12/2004 |
| JP | 2005-069728 | 3/2005 |
| JP | 2006-145499 A1 | 6/2006 |
| KR | 10-2001-0109019 | 12/2001 |
| KR | 10-2004-0008262 | 1/2004 |
| KR | 10-2005-0014797 | 2/2005 |
| KR | 10-2005-0037398 | 4/2005 |
| WO | 03/001423 | 1/2003 |
| WO | 2006/118420 | 11/2006 |

* cited by examiner

REMOTE-MEDICAL-DIAGNOSIS SYSTEM METHOD

CROSS REFERENCE TO RELATED APPLICATIONS

This application claims the benefit of International Application No. PCT/KR2008/002262, filed Apr. 11, 2008, and claims the benefit of Korean Application No. 10-2007-0040657, filed Apr. 12, 2007, the disclosures of all of which are incorporated herein by reference.

TECHNICAL FIELD

The present invention relates to a remote medical-diagnosis system and a method thereof.

BACKGROUND ART

The present invention is related to Korean Patent Application No. 10-2005-0036983, filed on Apr. 30, 2005, titled "A bio-disc, a bio-driver apparatus, and an assay method using the same"; Korean Patent Application No. 10-2005-0038765, filed on May 6, 2005, titled "A digital bio-disc, a digital bio-disc driver apparatus, and an assay method using the same"; Korean Patent Application No. 10-2005-0057513, filed on Jun. 28, 2005, titled "A bio DVD drive apparatus, and an assay method using the same"; Korean Patent Application No. 10-2005-0128469, filed on Dec. 21, 2005, titled "A bio memory disc, a bio memory disc drive apparatus, and an assay method using the same "; and Korean Patent Application No. 10-2006-0073597, filed on Aug. 2, 2006, titled "A thin film chemical assay apparatus and an assay method using the same".

One of the filed inventions provides: a micro valve to control flow of a fluid essential for a Lab-On-a-Chip system; a method of assaying bio substances; a bio-disc on which an assay apparatus is integrated; and a drive apparatus to control operation of the bio-disc.

Another one of the filed inventions provides a remote medical-diagnosis apparatus conveniently used by doctors and patients by assaying data measured using an assay device (assay site) by a detector combined with a converter which includes an optical measurement device, an electrochemical measurement device, a fluorescent measurement device, an impedance measurement device, or an image sensor device; converting the data into a digital value; and transmitting the result via a communication network such as the Internet.

Another one of the filed inventions provides a solid substrate (or solid carrier) in which channels as a fluid flow path, a chamber as a buffer reservoir, a hole connecting the channels, and an assay site with biomolecular arrays immobilized thereon are integrated, a valve used to open and close the hole connecting the channels, at least one preparation chamber for preparing serum or DNA samples from blood, an amplifying chamber for amplifying the DNA samples, various enzymatic functions, and configurations of the chambers.

Another one of the filed inventions provides a method of representing a product identification (ID) indicating a model number or a version of a bio-disc, on the bio-disc using a barcode pattern.

Furthermore, another one of the filed inventions provides a memory embedded wireless RF IC (or electronic tag) included in the bio-disc in order to store a protocol for a Lab-On-a-Chip, an assay algorithm, standard control values for assaying, positional information on assay sites, bioinformatic information, information related to self-diagnosis, bio-disc driver software, educational information on clinical assays for patients, a variety of web sites and links enabling a patient at a remote location to communicate with a doctor or hospital at a remote location based on his/her diagnosis result, encrypted personal information, history, or the like.

The wireless RF IC is an information-storing device for radio frequency identification (RF ID) replacing the barcode with a semiconductor chip, and includes an antenna and a semiconductor chip.

If information on a product such as date of production and product ID is recorded to the RF IC and the RF IC is attached to the product, the information can be identified wirelessly using a RF ID reader.

An animal RF ID is implanted to the animal or attached to the skin of the animal and includes a unique identification number. The RF ID and the RF IC are made based on international standards, such as ISO 11784 and ISO 11785, which are well known in the art, or the modifications thereof.

Since encrypted personal information and the product ID of the bio-disc are stored in the RF IC, they are not available for a non-authorized person.

In addition, information on species, age, place of origin, etc., of the animal is recorded to a tag which is attached to the animal RF ID, and thus, the information may be identified by a wireless RF ID reader.

Since the history of an animal can be tracked using the animal RF ID, when an animal disease such as mad cow disease, foot-and-mouth disease, bird flu, etc., occurs, efficient measures for the disinfection of the animal may be taken within a short period of time. Information on the raising, slaughtering of the animal and the processing and circulation of the meat of the animal can be obtained and be accurately revealed to customers.

The animal RF ID can also be applied to agricultural products and a food history tracking system, thereby providing customers with accurate information on food.

In addition, the types of diseases which can be detected by the bio-disc, according to a version of the bio-disc, can be stored in the wireless RF IC.

Information stored on the wireless RF IC is transferred to a bio drive apparatus via a wireless communication.

According to another one of the filed inventions, the assay site of the bio-disc includes a reference line (or reference spot) and a plurality of test lines (or test spots), and a concentration of a sample may be quantitatively measured using the biosensor based on a difference of relative reaction intensity.

Remote medical-diagnosis systems to diagnose human diseases by a remote doctor via a communication network are known in the art. For example, a remote diagnosis service has been conducted by converting data, such as blood pressure, pulse, and medical video Information, obtained from a patient into digital signals and transmitting the digital signals to a remote doctor.

A remote medical-diagnosis system capable of measuring a blood pressure or a pulse of a patient, storing the result in a storing device, and monitoring the result, in a remote area using a communication means, is disclosed in U.S. Pat. No. 4,889,132 (Dec. 26, 1989) titled "Portable automated blood pressure monitoring apparatus and method" and U.S. Pat. No. 4,712,562 (Dec. 15, 1987) titled "Outpatient monitoring systems".

A remote medical-diagnosis system including transmitting video images of a patient, which are obtained by computerized axial tomography (CAT) or magnetic resonance imaging (MRI), to a remote doctor, and a diagnosing is disclosed in U.S. Pat. No. 4,764,870 (Aug. 16, 1988) titled "System and method for remote presentation of diagnostic image information" and "Medical image information transmission system" (JP 02-218336; 1990-08-31).

A remote diagnosis system including converting an X-Ray into FM and transmitting the data to a remote area is disclosed in "X-Ray picture transmitter" (JP 59-047872; 1984-03-17).

A system including checking the daily state of a patient's health using a home health care system, and transmitting the result to a remote storing device or a remote doctor via a communication network is disclosed in a European Patent titled "Apparatus for monitoring and signaling system" (CA 1153441; 1983-09-06).

A remote medical-diagnosis system including measuring body temperature, blood pressure, etc., of a patient and storing in or transmitting the measured results to a remote area is disclosed in a Japanese Patent titled "Health meter" (JP 57-008418; 1982.01.16).

A remote medical system transmitting biological signals of a patient to a remote doctor is disclosed in Japanese Patent titled "System for transmitting signals from a living body" (JP 52-020050; 1977.02.15).

In addition, a remote diagnosis system in which a patient at home applies an electronic stethoscope to his/her body according to instructions of a remote doctor is disclosed in a Japanese Patent titled "Remote stethoscopy system" (JP 54-114008; 05.09.1979).

A remote medical-diagnosis system including inputting a patient's ID, measuring blood pressure, pulse, weight, an electrocardiogram, etc., transmitting the measured data to a remote health control apparatus using a communication network, and receiving diagnosis results is disclosed in a Japanese Patent titled "Health control apparatus" (JP 63-21870, 1988.02.03).

A remote diagnosis can be conducted according to conventional remote medical-diagnosis systems by which a doctor provides a patient with a text, voice, or video medical consultation service via a communication network including the Internet, a doctor gives instructions as how to use an apparatus for medical examination to a patient and analyzes measured data of the apparatus for medical examination so as to provide a remote diagnosis in real time, or a doctor in a remote area stores data measured using an apparatus for medical examination via a server of a hospital, analyzes the data, and notifies a patient of the diagnosis result.

However, such conventional remote medical-diagnosis systems have problems as follows.

Firstly, a device for blood assay is so expensive that only central laboratories and hospitals can purchase the device for blood assay and so complicated that only trained experts can handle the device for blood assay. Thus, an urgent sample cannot be immediately analyzed since the sample needs to be transported to the central laboratories and hospitals. This is regarded as a "passive type" remote medical-diagnosis system, and in this system, the patient should visit the hospital and consult with the doctor for most of the examinations using a blood sample, and receive at home the diagnosis results of the examinations conducted based on the blood sample from a remote doctor.

Secondly, if there are many other patients waiting, a patient should wait for a doctor to use an apparatus for medical examination according to real time instructions of the doctor, the transmitting of the measured data to the doctor in real time, and the receiving of a remote diagnosis result even if the patient has the apparatus for medical examination. Thus, in this "real time apparatus for medical examination" or remote medical-diagnosis system type, the patient waits for the doctor.

Thirdly, a "passive type" remote medical-diagnosis system in which a patient should wait for a doctor's diagnosis after transmitting data measured using an apparatus for medical examination and a bioanalytical device to the doctor in a remote area even if the patient has the apparatus for medical examination and the bioanalytical device, is very inconvenient. If the patient spends time waiting for the doctor or pays for simple or frequent examinations, using the remote medical-diagnosis system may be inconvenient.

Fourthly, a patient cannot choose a medical expert (a doctor, a hospital, a pharmacy, or a pharmacist) in the conventional remote medical-diagnosis system. That is, the patient who signs up to the conventional remote diagnosis system does not have rights to select a doctor or a pharmacist. However, the patient should have rights to have high-quality service from qualified doctors or pharmacists.

Fifthly, most of the conventional remote medical-diagnosis systems are conducted between a patient and a doctor. However, simple consultation with a pharmacist and medicine purchased according to the pharmacist's prescription may be enough for light diseases such as flu virus or a headache. Thus, there is a need to connect the patient with the pharmacy as well as the hospital in the remote medical-diagnosis system. In addition, information on the patient's constitution analyzed using the bioanalytical device should be transmitted to the pharmacy as well as the hospital to obtain a personalized prescription and purchase a personalized medicine. That is, there is a need for a remote medical-diagnosis system for personalized medicine.

Sixthly, a conventional remote medical-diagnosis system is used after a patient signs up to the system, receives a password, and agrees to the rules and regulations. However, the sign up process and authentication process are complicated, and there is a risk of medical accidents caused by the misuse and leakage of the password. In addition, since patients are mainly the elderly, they are not easily accustomed to the complicated sign up process and authentication process, or they often lose their passwords.

DETAILED DESCRIPTION OF THE INVENTION

Technical Problem

The present invention provides a remote medical-diagnosis system including:

a bio-disc or a biochip performing biological, chemical or biochemical reactions with a sample, and having a barcode or radio frequency integrated circuit (RF IC);

a bioanalytical device analyzing results of reactions performed by the bio-disc or the biochip and including a reader reading the barcode or the RF IC to authenticate the bio-disc or the biochip or recording the measured data to the RF IC regardless of a connection with a remote diagnosis server;

a virtual doctor residing as a software on a user's terminal, the virtual doctor providing a user with guidelines and instructions as how to use the bioanalytical device, and providing the user with a consulting service, a diagnosis unit analyzing the measured data using mathematical calculations and outputing results of a diagnosis;

a user's terminal providing the user with a consulting service from a medical expert or a virtual doctor;

a medical expert's terminal providing the user with a consulting service; and a remote diagnosis server connecting the user with the medical expert during periodic medical consultations, connecting the user with the virtual doctor except during periodic medical consultations, blocking connection between the user and the virtual doctor if a periodic medical consultation term has elapsed; and a method of performing the remote medical-diagnosis.

BEST MODE

Figure 1:
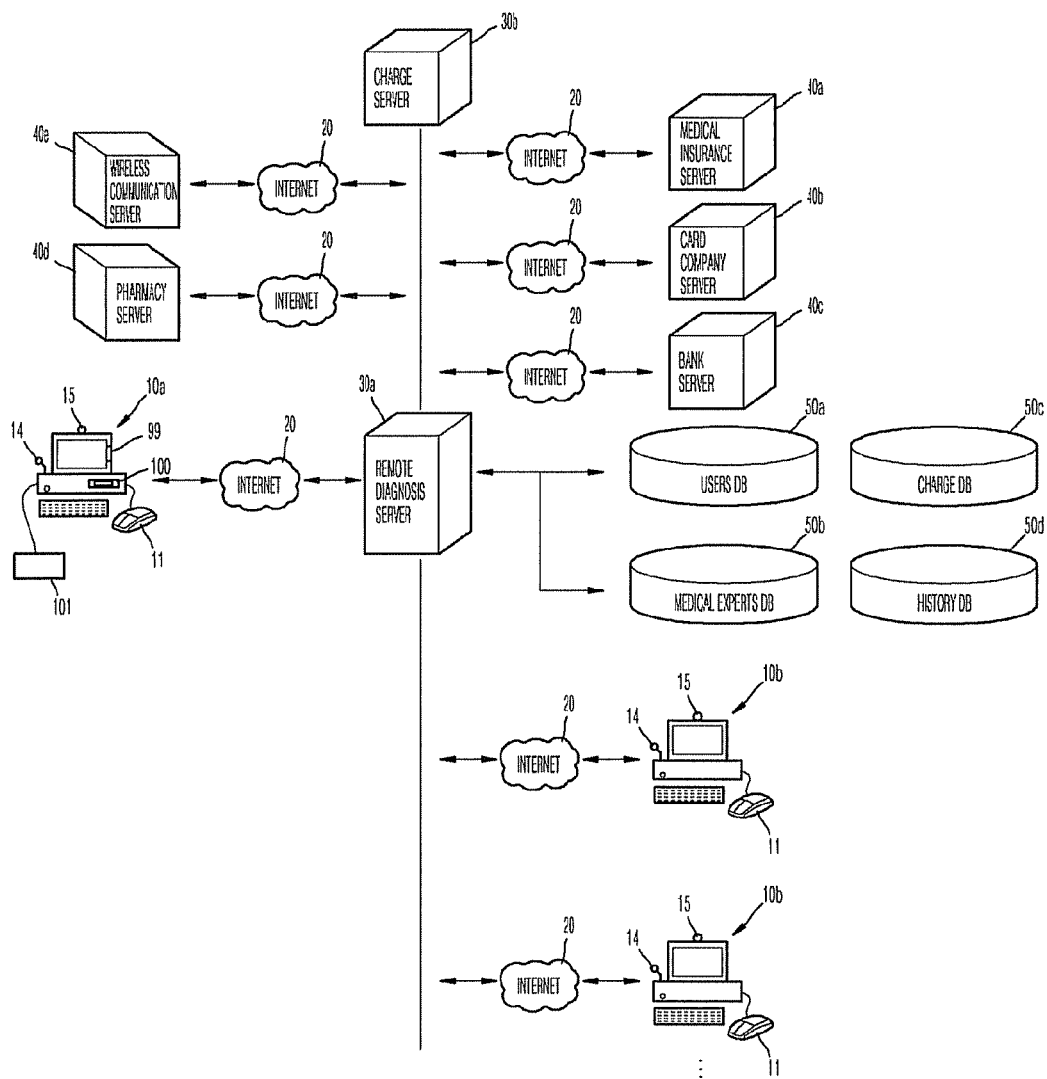
FIG. 1 shows a block diagram of a remote medical-diagnosis system that uses the Internet, according to an embodiment of the present invention.

The present invention provides a remote medical-diagnosis system and a method of operating the remote medical-diagnosis system.

A "bio-disc" may include a bio-disc, a digital bio-disc, a thin film chemical analysis device or a bio memory disc on which a lab-on-a-chip, which can be applied to a variety of diagnostic analysis devices such as a nucleic acid hybridization analysis device, a bio material analysis device, a device analyzing a patient's constitution for personalized medicine, a urea analysis device, a blood analysis device, an environmental pollution (air pollution, water pollution, food-born pathogen) analysis device, a biochemical analysis device, or an immunoassay device, is integrated.

The water pollution may be measured by analyzing the degree of heavy metal pollution, the concentration of bacteria, etc., in water. Pollutions by organic mercury, a cyan compound, organic phosphorus, cadmium, arsenic, phenol, copper, lead, and chrome are analyzed to measure the heavy metal pollution. The content of $SO_2$, dust (TSP), carbon monoxide (CO), nitrogen dioxide ($NO_2$), hydrocarbon (HC), ozone ($O_3$), lead (Pb) in the air may be analyzed to measure the air pollution.

A "bio drive" is a device including a biosensor which controls operations of a bio-disc and measuring data and analyzing the data by allowing loading, inserting, mounting, or integrating of the bio-disc.

A "biochip" includes a DNA chip, a lab-on-a-chip, a protein chip, a rapid test kit or a rest strip.

A "medical expert" includes a doctor, a hospital, a pharmacist, a pharmacy, or a medical consultant.

An "environmental expert" is a person who monitors and controls environmental pollution (air pollution and water pollution).

A "diagnosis expert" includes a medical expert and an environmental expert.

A "user" includes a "patient" and a "bio robot" which collects environmental pollutants and injects them into a bioanalytical device.

In order to measure natural conditions affected by environmental pollution or air pollution, the bio robot periodically collects water or air or measures temperature or tree leaf color and automatically loads them on a bioanalytical device, and then a remote diagnosis service can be provided by a remote medical-diagnosis system. Such a bio robot may be installed nationwide and operated by solar energy.

A "biochip analysis apparatus" is an apparatus including a biochip which measures data and determines results of the data by allowing loading, inserting, mounting, or integrating of the biochip.

The biochip analyzes a sample obtained from a user in order to diagnose a disease, test the immune system, detect genetic diseases, analyze biomaterials, or analyze the user's constitution for personalized medical treatment.

A "bioanalytical device" includes the bio drive and biochip analysis apparatus, and obtains data measured by a biosensor.

A "medical data" includes diagnosis results, details on the diagnosis, medical examination data (e.g., data measured by devices such as X-RAY, computerized axial tomography (CAT), magnetic resonance imaging (MRI), etc., and data measured using bioanalytical devices), a check list, a charges list, past medical history, past medicine prescription records, and past medical records.

An "apparatus for medical examination" includes a thermometer, a sphygmomanometer, a stethoscope, a body composition analyzer, an alteriosclerosis detector, an ultrasonic scanning apparatus, an urianalyzer, a pulse monitor, a blood sampling device, an electrocardiogram, an X-Ray apparatus, an oxymeter, a dementia detecting apparatus, a computerized axial tomography (CAT) apparatus, a magnetic resonance imaging (MRI) apparatus, a capsule endoscopy, a magnifier, a magnifier with a camera, a medical instrument, a bio signal detecting apparatus, and a bio shirt having a function of detecting a bio signal (diabetes, obesity, blood pressure, pulse, an electrocardiogram, body temperature, or the like).

The internal body organs of a patient can be observed via the capsule endoscopy after the patient swallows the capsule endoscopy. The capsule endoscopy transmits images taken inside the patient's body to the outside of the body so that the medical expert can observe the inside of the patient's body.

The capsule endoscopy is disclosed in U.S. Pat. No. 4,217,045 (Aug. 12, 1980) titled "Capsule for photographic use in a walled organ of the living body" and U.S. Pat. No. 6,855,111 (Feb. 15, 2005) titled "Capsule endoscope".

A bio shirt is a 'wearable computer' to which various sensors are attached to transmit heart beats, respiration rate, exercise volume, etc., to the hospital in order to monitor health conditions in real time, and is disclosed in U.S. Pat. No. 6,985,078 (Jan. 10, 2006) titled "Wearable life support apparatus and method".

Hereinafter, the present invention will be described in more detail.

According to an embodiment of the present invention, there is provided a remote medical-diagnosis system including:

a bio-disc or a biochip performing biological, chemical or biochemical reactions with a sample, and having a barcode or radio frequency integrated circuit (RF IC);

a bioanalytical device authenticating the bio-disc or the biochip by analyzing results of reactions performed by the bio-disc or the biochip and including a reader reading the barcode or the RF IC to authenticate a product identification (ID) of the bio-disc or biochip, and recording measured data corresponding to the results to the RF IC;

a user's terminal comprising a transmitter transmitting the measured data and the product ID of the bioanalytical device to a remote diagnosis server via a communication network, and a first consulting service unit providing a consulting service from a medical expert;

a virtual doctor residing as a software on the user's terminal, the virtual doctor comprising a guideline unit to provide a user with guidelines or instructions as how to use the bioanalytical device, and a diagnosis unit self-analyzing the measured data using mathematical calculations and outputting a diagnosis result;

a medical expert's terminal comprising a receiver receiving the measured data via the communication network, and a second consulting service unit providing the user with a consulting service; and a remote diagnosis server comprising a second authentication unit authenticating the product ID of the bioanalytical device, an ID registration unit registering and storing the product ID of the bioanalytical device authenticated by the second authentication unit, an expert selecting unit connecting the user with the medical expert during periodic medical consultations and connecting the user with the virtual doctor except during periodic medical consultations, a connection blocking unit blocking connection between the user and the virtual doctor if a periodic medical consultation term has elapsed, and a priority connection unit connecting the user with the medical expert upon receiving a signal requesting for a priority connection even if the periodic medical consultation term has not elapsed.

The bioanalytical device includes an authentication unit authenticating the bio-disc or biochip, and a recording unit recording measured data to the RF IC.

The product ID of the bioanalytical device that is being used may further be recorded to the RF IC.

The signal requesting for a priority connection may be a signal generated by the virtual doctor when the virtual doctor recognizes abnormal conditions based on that the measured data or a variation rate of the data is greater than a cutoff level as determined by the medical expert.

According to another embodiment of the present invention, there is provided a remote medical-diagnosis system and a method of operating the remote medical-diagnosis system, the remote medical-diagnosis system including:

a graphic user interface (GUI) real-time monitoring the status of operation and progress of a bioanalytical device connected to a user's terminal, controlling on/off of the bioanalytical device or an apparatus for medical examination connected to the user's terminal, displaying a rate of progress of the bioanalytical device, or displaying measured data in terms of numbers, in a graph, or a high-medium-low form, providing a user with a medical consultation from a medical expert via the Internet upon request by the user, after the user is authenticated using an user identification means, providing a window displaying a DVD movie, a TV program, a DMB broadcast, or a multimedia program, a window for Internet surfing or computer applications, or a telephone communication means, communicating medical data to a medical expert and a remote diagnosis server via a communication network, providing a diagnosis service from a virtual doctor, providing a remote diagnosis service from a virtual reality doctor, analyzing an environmental pollutant in a remote area, or providing a hopping medical diagnosis service, automatically purchasing medicine, according to a medical prescription, based on the diagnosis determined by the medical expert, paying fees for the remote diagnosis service using electronic money, a credit card, a check card, or an electronic medical card, storing events which occurred in the user's terminal during the remote diagnosis, managing data files obtained from the bioanalytical device and apparatus for medical examination, a check list, a charges list, medical data based on date, type, and directory, or recording the diagnosis results to an RF IC of the bio-disc, an animal RF ID, or an RF IC of the biochip (or electronic tag); and a card reader as an option.

The card may be one of a check card, a debit card, an electronic medical insurance card, a credit card, and a cellular phone.

The card may be a contact card or a non-contact card.

The card reader may be embedded in a rim around a screen of a monitor or keyboard of the user's terminal.

Diagnosis results provided by the medical expert and the virtual doctor and an ID of the medical expert may be stored in the RF IC.

Since the ID of the medical expert is stored in the RF IC, the medical doctor who makes a diagnosis for the bio-disc or the biochip can be identified.

The diagnosis results made by the virtual doctor may be automatically stored in the remote diagnosis server through the GUI.

A past diagnosis history previously obtained by the virtual doctor or medical expert may be received from the remote diagnosis server and cumulatively stored in the to RF IC.

The ID and password of the user required for the sign up and authentication of the remote diagnosis server may be stored in the RF IC so that the bio-disc and biochip can be personally encrypted.

In addition, the ID and password of the user may be transmitted to, stored in and managed by the remote diagnosis server to be used for access of the remote diagnosis server through the GUI.

In the remote medical-diagnosis system, the bioanalytical device performs analysis of the bio-disc or the biochip connected to the user's terminal, and may include a barcode reader which reads a barcode on the bio-disc or the biochip or a RF ID reader which reads an animal RF ID chip, a RF IC of the bio-disc, or a RF IC of the biochip.

By the graphic user interface (GUI), animal authentication, bioanalytical device authentication, bio-disc authentication, or biochip authentication may be performed by providing the product ID read by the RF ID reader or the barcode reader to the remote diagnosis server.

According to another embodiment of the present invention, an authentication of the apparatus for medical examination or the bioanalytical device may be performed by reading the product ID of the apparatus for medical examination or the bioanalytical device from a memory or the RF IC and transmitting the product ID to the remote diagnosis server through the GUI.

If the authentication of the product ID fails, the GUI is deactivated or the apparatus for medical examination or the bioanalytical device does not operate.

The GUI determines that the product which fails the authentication is not genuine.

The product ID may be a serial number of the product, and the apparatus for medical examination or the bioanalytical device which fails authentication may not operate since an operational software cannot be downloaded from the remote diagnosis server.

The user's terminal may further be connected to a local server for remote communications, a home network system, or a home network system cooperating with a user's home appliances, or include them.

In addition, the bioanalytical device may be connected to a cellular phone via a USB cable for the remote communications of the user's terminal.

A home network system for a home health care system is disclosed in U.S. Pat. No. 4,259,548 (Mar. 31, 1981) titled "Apparatus for monitoring and signaling system" and U.S. Pat. No. 4,281,394 (Jul. 28, 1981) titled "Monitoring and signaling system including apparatus for processing binary signals having multiple messages".

The user's terminal may be a computer connected to the Internet, a TV connected to the Internet, a home appliance connected to the Internet, or a portable communication apparatus.

The bioanalytical device may qualitatively and quantitatively analyze blood, urea, or bio-materials so as to perform various disease-related tests to detect cancer, blood sugar, blood type, body fat, obesity, viscosity of blood, blood pressure, cardiovascular diseases, oxygen saturation in blood, a patient's constitution for personalized medicine, Alzheimer's, dementia, liver disease, myocardial infarction, AIDS, environmental pollution, venereal diseases, pregnancy, genetic diseases, cholesterol GOT, GPT, or the like.

In the analysis of urea, the bioanalytical device may analyze leucocyte, blood, protein, nitrite, pH, specific gravity, glucose, ketone, ascorbic acid, urobilinogen, bilirubin, body fat, or blood pressure.

The bioanalytical device includes a lab-on-a-chip employing enzyme-linked immunosorbent assay (ELISA), a lab-on-a-chip employing a rapid test; a lab-on-a-chip for tests to detect food-born pathogens, residual antibiotics, residual agrichemicals, gene manipulated food, air pollution, water pollution, allergy, paternity, meats and place of origin of the meat; and a small-sized or thin film analyzer diagnosing and detecting a small amount of bio-materials or chemicals in a fluid.

The bio-materials may be selected from the group consisting of DNA, oligonucleotide, RNA, PNA, ligand, a receptor, an antigen, an antibody, milk, urea, saliva, hair, an agricultural sample, a plant sample, a sample for environmental tests (wastewater and air), a meat sample, a fish sample, a bird sample, a livestock sample, a food sample, oral cell, a tissue sample, sperm, protein, or living material.

According to another embodiment, the bioanalytical device performs tests for food-born pathogens in food establishments or restaurants and transmits the data to the remote diagnosis server.

The bioanalytical device may further include a sanitation level display device which displays a sanitation level of restaurants evaluated by an environmental expert connected to the remote diagnosis server or a food poisoning analysis software residing on the remote diagnosis server based on the obtained data.

The sanitation level may be represented by grades such as excellent, good, and poor or by numbers.

The sanitation level display device may be publicly installed at an upper portion of a door of the food establishments or restaurants.

The bioanalytical device may access the user's terminal through an input/output unit in a wired or wireless manner, be integrated in the user's terminal, or attached to and detached from the user's terminal.

The user's terminal may access a remote terminal of a doctor, a hospital, or a pharmacy via a remote diagnosis server on the Internet in a wired or wireless manner. The remote diagnosis server may be connected to servers of a bank, a card company, a pharmacy, and a medical insurance company, to charge the user; or connected to a wireless communication server to send a charges list and details of the remote diagnosis to the user.

The apparatus for medical examination may access the user's terminal through an input/output unit in a wired or wireless manner, be integrated in the user's terminal, or attached to and detached from the user's terminal.

Medical data of the user (diagnosis results, details of the remote diagnosis, and examined data), which is stored in the remote diagnosis server, may be co-owned with the medical experts.

Thus, the medical expert may read past medical history of a patient who visited a hospital from the remote diagnosis server, during an off-line interview with the medical expert. In addition, the medical expert may further store the diagnosis result obtained from the off-line medical examination and details of the remote diagnosis in the remote diagnosis server.

In the remote medical-diagnosis system, the GUI provides information to the user, the information selected from the group consisting of information on a protocol of the bioanalytical device, information on an assay algorithm, information on a standard control value for detection or positional information on assay sites, medical information, biological information, information on self-diagnosis, information on device driver software and patient education, method of using the bioanalytical device and examination device, and information on web sites and links which can be remotely connected to a doctor and hospital based on the diagnosis results, information on the bioanalytical device, or information on the apparatus for medical examination.

In the remote medical-diagnosis system, the GUI may include at least one function selection button selected from the group consisting of "assay start" button to control the bioanalytical device, "assay stop" button, "power on/off" button, "eject or unloading" button, "remote transmittance" button, "remote receiving" button, "diagnosis results confirmation" button, "diagnosis and medical practice records confirmation" button, a "VR ON/OFF" button to set up a virtual reality remote diagnosis mode, a "check list" button, a "Qs & As" button, a "charges list confirmation" button, a "payment authorization" button, and a "camera environment set up" button.

In the remote medical-diagnosis system, the GUI comprises, a progress rate display window displaying a rate of progress of the bioanalytical device;
  a button selecting the bioanalytical device;
  a button selecting an apparatus for medical examination;
  a chat window;
  a medical service window displaying a medical service in order to display measured data of the bioanalytical device in terms of numbers, in a graph, or a high-medium-low form, display measured data of the medical examination in terms of numbers, in a graph, or a high-medium-low form, display diagnosis results of the bioanalytical device or the apparatus for medical examination, display the check list, display questions and answers, display status of the user while the user is using the bioanalytical device or apparatus for medical examination in real time, display how to use the bioanalytical device or apparatus for medical examination, as provided by the medical expert, display the charges list, control the bio robot, display medical data or medical prescription received from the medical expert, play a DVD video or TV program, display image for Internet surfing or paper work, provide telephone buttons and video image while using an Internet video phone, input information related to the remote diagnosis service and the GUI and inform the user of additional messages, or display information received by a messenger program to the user;
  a medical expert selection window;
  a hospital selection button and a pharmacy selection button; and
  a "control assignment" button in order to assign a "remote control right" of the GUI to the selected medical expert.

The bio-disc or the biochip loaded on the bioanalytical device is unloaded by an eject button.

In the remote medical-diagnosis system, the GUI displays at least one medical expert provided by the remote diagnosis server to the user, and provides a medical consultation service after the user selects a medical expert.

The GUI transmits medical data or questions of the user to the selected medical expert by clicking the "remote transmittance" button when the analysis of the bioanalytical device or apparatus for medical examination is completed.

The GUI may be activated only when the electronic medical insurance card is inserted into the card reader and information on the medical insurance is read by the GUI.

The GUI may be automatically activated on the monitor of the user's terminal when the bio-disc or the biochip is loaded on the bioanalytical device.

The medical expert's terminal may include a prescription-generating unit which generates a medical prescription by the medical expert.

In addition, the remote diagnosis server may include a medicine preparation request unit which receives the prescription and requests a pharmacist to prepare medicine according to the prescription and transmits the medicine, and a payment unit by which the user pays the fees for the preparation and transmission of the medicine with electronic money or a card.

The charging process for the remote diagnosis service by the GUI includes reading information on the user from a card inserted into the card reader, transmitting the information on the user's card to a charging server when the user clicks a "payment authorization" button, and informing the user of success of the payment while sending the charges list (basis on the charging, diagnosis results, medical examination, and consultation hours).

The charges and charges list may further include fees for medicine.

The GUI may transmit commands to monitor the status of operation and progress of the bioanalytical device in real time through an input/output unit in a wired or wireless manner, receive analysis results (measured data of the bioanalytical device), and control operation of the bioanalytical device.

The GUI may transmit a command for automatically ejecting or unloading the bio-disc or the biochip if they are loaded on the bioanalytical device without a blood sample or send a warning message to the user.

The GUI may further include a validity checking unit transmitting a command for automatically ejecting or unloading a bio-disc from the bioanalytical device when a bio-disc is unidentified by the bio drive, a previously used bio-disc is loaded, or the valid period of the bio-disc is over, or sending a warning message to the user.

The GUI may further include a validity checking unit transmitting a command for automatically ejecting or unloading a biochip from the bioanalytical device when a biochip is unidentified by the biochip analysis apparatus, a previously used biochip is loaded or the valid period of the biochip is over, or sending a warning message to the user.

If the user requests for an assay stop or an un-loading of the bio-disc or the biochip while the bio-disc or the biochip is analyzing the sample, the GUI may include an assay stop process unit which keeps processing the analysis, sends a warning message to the user, or demands for login information (personal ID and password).

That is, the GUI transmits a command for ejecting or unloading from the bioanalytical device, if the password is correct in order to accept the request for un-loading or the assay stop by the user, and if the user requests for an assay stop or an un-loading of the bio-disc or the biochip while the bio-disc or the biochip is analyzing the sample.

If the assay of the bio-disc or the biochip is stopped by the password, the assay stop may be included in the history management list to be stored in the RF IC or stored in the remote diagnosis server.

The GUI may include a RF IC reader which provides the user with information, read from the RF IC, selected from the group consisting of the types, version, date of manufacture, and validity period of the bio-disc or the biochip loaded on the bioanalytical device, a diagnosable disease list, user precautions, details of a history management list, medical data, and next examination date. The history management list includes past diagnosis results.

That is, the GUI provides the user with information read from the RF IC, such as medical data, details of a history management list, and next examination date, regardless of online connection when the used bio-disc or the biochip is loaded on the bioanalytical device.

In the GUI, information on medical data, details of a history management list, and next examination date may be accessed by further including a password authentication process using a password stored in the RF IC when the used bio-disc or the biochip is loaded on the bioanalytical device.

The GUI further includes an information access unit which transmits a product ID or a product serial number read from the RF IC of the bio-disc or the biochip loaded on the bioanalytical device to the remote diagnosis server, and provides the user with information, received from the remote diagnosis server, selected from the group consisting of the types, a version, date of manufacture, and validity period of the products, a diagnosable disease list, user precautions, details of a history management list, medical data, and next examination date, after an authentication of a password by matching a password stored in the remote diagnosis server.

That is, the GUI provides the user with medical data, details of a history management list, and next examination date, received from the online remote diagnosis server when the bio-disc or biochip that is being used is loaded on the bioanalytical device.

In the GUI, information on medical data, details of a history management list, and next examination date may be accessed by further including a password authentication process using a password stored in the remote diagnosis server when the bio-disc or biochip that is being used is loaded on the bioanalytical device.

The GUI enhances information on images of assay sites received from the bioanalytical device to calculate a difference of a relative reaction strength between a standard line/spot and a test line/spot, and then remotely transmits the calculated data as measured data, remotely transmits the enhanced image information as measured data, or remotely transmits original image information as measured data.

The enhancement of the image information may be conducted by histogram equalization, contrast control, image enhancement technology or noise eliminating technology used for image processing, which is disclosed in "Digital image processing", 2nd edition, Rafael C. Gonzalez and Richard E. Woods, Prentice Hall, 2002".

The GUI operates and controls the bioanalytical device according to a protocol of the bioanalytical device corresponding to the product ID, an assay algorithm, a standard control value for detection or positional information on assay sites.

The apparatus for medical examination may include a memory or a RF IC (or electronic tag) storing a protocol for the apparatus for medical examination, an assay algorithm, a standard control value for detection, self-diagnostic information, information on driver software of the apparatus for medical examination and patient education, a model number and a version of the apparatus for medical examination, a manufacturer of the apparatus, date of manufacture of the apparatus, information on web sites and links which can be remotely connected to a doctor and hospital, encrypted personal information to communicate with the user's terminal in a wired and wireless manner.

The GUI may be upgraded by automatically downloading operational software through the Internet when the GUI does not include a protocol of the bioanalytical device and the apparatus for medical examination corresponding to the product ID of the bioanalytical device and the apparatus for medical examination, a standard control value for detection, or positional information on assay sites.

The GUI records a personal ID and a password of the user, the product serial number (product ID) of the bioanalytical device and the apparatus for medical examination, the product serial number (product ID) of the bio-disc or the biochip, and a date of use, in the user's terminal or the RF IC as a history management list, or remotely transmits the details of the history management list to an after service (A/S) related server of the manufacturer or the remote diagnosis server through the communication network when using the bioanalytical device and the apparatus for medical examination.

When an invalid bio-disc or biochip is used, the GUI informs the user of the invalid use by sending a warning message, stores the invalid use in the RF IC, or transmits details of the history management list with the information on time and the product serial number (product ID) to the A/S related server of the manufacturer of the bioanalytical device or the remote diagnosis server through the communication network.

The GUI further includes a humidity checking unit which notifies the user of excess humidity by sending a warning message when the bio-disc or the biochip is exposed to excess humidity by analyzing an image of a humidity sensing chamber, or stores the excess humidity in the RF IC or transmits the excess humidity with information on time and the product serial number (product ID) to the A/S related server of the manufacturer of the bioanalytical device or the remote diagnosis server through the communication network.

The GUI receives the image of a humidity sensing chamber and validity information from the bioanalytical device. The humidity sensing chamber includes a humidity indicator card that can instantly determine whether the humidity in a closed or sealed space in the product exceeds a limit. For example, if the humidity indicator card turns pink from blue, the product has been exposed to humidity or soaked in a liquid.

The validity of the bioanalytical device may be recognized by reading information on the date of manufacture stored in the RF IC (electronic tag) of the bio-disc and the biochip.

Historical details such as humidity exposure history, invalid use history, or assay stop history using a password may be stored in the RF IC.

The GUI displays a rate of progress of main processes of the bioanalytical device, such as a preparation process, an amplification (or PCR) process, a hybridization process and an antigen-antibody reaction, as a percentage (%), a bar graph, or a pie graph, or displays time left.

The GUI further includes an automatic notifying device which notifies the user with information on a medical examination schedule using the bioanalytical device and the apparatus for medical examination, a hospital visit schedule, or a medicine intake schedule which are received from the remote diagnosis server using a message transmittance means.

The GUI further includes an automatic notifying device which notifies the user with information on a medical examination schedule using the bioanalytical device and the apparatus for medical examination, a hospital visit schedule, or a medicine intake schedule which are automatically generated using a message transmittance means.

The message transmittance means may be an e-mail, a SMS message/voice message/video message via a communication network, or messenger, or a SMS message/voice message/video message via a medical service window.

The GUI provides a telephone panel button including ten keys or a video image of a counterpart via telephone communication means.

The telephone panel further includes an emergency speed dial button and a personal phone book.

The GUI receives the check list from the medical expert via a communication network or resends the filled out check list to the medical expert.

The GUI further includes a fingerprint reading software, a voice recognition software, a face recognition software, a lip recognition software, or a pupil recognition software to automatically authenticate an identification of the user.

In this regard, a fingerprint reading device, a camera, or a microphone may be connected to the user's terminal, and the fingerprint reading device may be integrated with a mouse.

The GUI transmits the medical prescription generated according to the diagnosis result by the medical expert to the pharmacy for an automatic purchase of medicine, and automatically transmits the address of the user to the pharmacy for an automatic delivery of the medicine.

The remote diagnosis server displays pharmacies in the vicinity of the user's residence to the user, and the user may select a pharmacy.

The GUI informs the user of an expected arrival time of the medicine from the selected pharmacy using the message transmittance means for an automatic purchase of medicine, according to the medical prescription of the medical expert.

The GUI includes a virtual doctor which (i) displays the diagnosis results, obtained by analyzing data measured by the bio-disc, biochip, or apparatus for medical examination through mathematical calculations, on a medical service window in terms of numbers, in a graph, in a high-medium-low form, or by comparing the diagnosis results with a cutoff level, (ii) informs the user of the diagnosis results using the message transmittance means (iii) records the diagnosis results to the RF IC, and (iv) stores the diagnosis results in the remote diagnosis.

The virtual doctor is included as a software in the user's terminal including at least one camera, a microphone receiving the user's voice, a speaker which requests the user to correct the misuse of the apparatus for medical examination and bioanalytical device by analyzing video images taken by the camera, and provides guidelines and instructions, and a graphic means; and an algorithm for these process in order to monitor the user of the apparatus for medical examination or bioanalytical device.

In addition, the software of the virtual doctor may further include a voice recognition software which recognizes the voice of the user.

The GUI includes a statistics software which manages a disease history so as to manage a history of self-diagnosis results of the bioanalytical device or apparatus for medical examination, manage a change of the history, or periodically report the disease history to the remote diagnosis server.

The GUI allows the virtual doctor or medical expert to provide the patient with guidelines about blood sampling and injection of the sample into the bioanalytical device in real time.

In order for the virtual doctor or medical expert to provide the patient with guidelines about blood sampling and injection of the sample in real time, the state of blood sampling and injection of blood should be monitored in real time.

For the real time monitoring, the camera or bioanalytical device connected to the GUI may further include a monitoring unit which transmits information on the injection of the sample into the preparation chamber to the medical expert.

A method of detecting injection of a sample into a preparation chamber is disclosed in Korean Patent Application No. 10-2005-0038765 (May 6, 2005) titled "Digital bio-disc and digital bio-disc drive apparatus and method thereof". That is, in order to detect the injection of the sample, the preparation chamber includes an impedance measurement device, an image sensor device, or a light transmittance measurer.

The GUI detects whether serum of the blood sample injected into the preparation chamber of the bio-disc is normally separated by checking the state of serum (blood plasma) that is centrifuged or separated by a serum separation device, and informs the user of abnormal serum separation or stores a record of the abnormal serum separation in the history management list.

If the serum is not normally separated, the blood is not qualified or the blood sampling or the injection of the sample is not normally performed. Thus, the diagnosis results obtained therefrom are not reliable.

Generally, globules, which are heavier than serum, sink after centrifugation of blood and serum floats and has a straw color.

If the serum is normally separated, the volume of the serum is about ⅓ of the total volume of the blood, and the serum has a straw color. Information on the serum is received from the light transmittance measurer or image sensor of the bioanalytical device connected to the GUI.

For example, the degree of serum separation and the amount of separated serum may be measured by the light transmittance measurer of the bioanalytical device by transmitting a laser beam into the preparation chamber and measuring light transmittance in the preparation chamber using a light sensor, since serum has a higher light transmittance than globules, and the obtained data is transmitted to the GUI.

The degree of serum separation and the amount of separated serum may also be measured by the image sensor in the bioanalytical device that recognizes the preparation chamber, and thus normal separation of the serum and globules may be detected. Then, the obtained data is transmitted to the GUI.

The degree of serum separation and the amount of separated serum measured by the light transmittance measurer or the image sensor may be transmitted to the remote diagnosis server.

The amount of separated serum is important for quantitative analysis. The intensity of the reaction may be calculated in consideration of the amount of separated serum to improve the accuracy of the data for the quantitative analysis.

The GUI includes a hopping medical diagnosis service including mandatorily performing only the periodic medical consultations by the medical expert via a remote diagnosis and the non-periodic medical consultations by the virtual doctor by self-analyzing data obtained from the bioanalytical device or apparatus for medical examination, and informing the patient or remote diagnosis server of the diagnosis results.

The diagnosis results obtained by the virtual doctor may automatically be stored in the remote diagnosis server via the GUI.

The past diagnosis results obtained by the virtual doctor may be received from the remote diagnosis server and stored in the RF IC.

That is, the past diagnosis history of the patient or measurement history may be identified by reading the RF IC of the recently used bio-disc.

The periodic medical consultations may be performed once a month, once a six months, or once a year.

The GUI includes a hopping medical diagnosis service mandatorily performing a remote diagnosis with the medical expert even if the service is not the periodic medical consultations, if requested by the user, if abnormal conditions are detected by the virtual doctor, and if the diagnosis service with the virtual doctor is performed over a predetermined number of times, or after a predetermined period of time (e.g., 6 months) since the patient receives the last remote diagnosis service from the medical expert.

The GUI determines whether the bio-disc or the biochip is for an environmental pollution detection based on the product ID recognized by the RF IC (electronic tag) or the barcode.

The GUI determines whether the bioanalytical device or apparatus for medical examination is for an environmental pollution detection based on the product ID.

The GUI provides an environmental expert, instead of the medical expert, on the medical expert selection window, if the bioanalytical device or apparatus for medical examination is determined as an apparatus for an environmental pollution detection based on the product ID.

A remote control right of the GUI of the bioanalytical device for environmental pollution is assigned to the environmental expert or canceled.

The environmental expert accesses a terminal connected to the bioanalytical device and the apparatus for medical examination in order to obtain the remote control right of the GUI or the bioanalytical device. In this regard, the environmental expert presents an address of the terminal to be accessed via the remote diagnosis server or an environment monitoring server.

The GUI provides the remote diagnosis server or environment monitoring server with positional information of the bioanalytical device for environmental pollution detection, which is obtained by the GPS.

The positional information obtained by the GPS may be provided to the GUI by connecting a cellular phone with the bioanalytical device further including a positional information receiver.

If the remote control right of the GUI of the bioanalytical device is assigned to the environmental expert, the environmental expert remotely controls all functional buttons of the GUI or remotely controls motions of the bio robot.

The environment monitoring server may store information on environmental pollution of user's terminals distributed across the country. The bio robot may include a collection means and a loading means which periodically collects water or air to measure natural conditions affected by environmental pollution or air pollution and automatically loads the collection on a bioanalytical device, receive a remote diagnosis service of the environment via the remote medical-diagnosis system, be distributed nationwide, and operate using solar energy. The bio robot may further include a temperature sensor, an image sensor, or a light sensor which measures temperature in the vicinity of the bio robot or tree leaf color.

The bio robot may transmit signals obtained by the sensors to the bioanalytical device via a wireless communication means.

The GUI includes a statistics software which manages pollution history so as to manage the history of self-diagnosis results of the bioanalytical device or device for environmental pollution detection, manage a change of the history, periodically report the disease history to the environment monitoring server or the remote diagnosis server, or inform the environmental expert of abnormal conditions using the message transmittance means.

In the GUI, the virtual doctor or environmental expert provides the user with guidelines about collecting pollutants and injection of the environmental pollutant into the bioanalytical device.

The present invention also provides a method of performing a remote medical-diagnosis using a remote medical-diagnosis system according to the present invention, the method including: installing a GUI program downloaded from a web site so as to provide a remote diagnosis service in the user's terminal; inserting a card into a card reader for signing up after the GUI program is operated; signing up and performing authentication by transmitting information on the user's card read by the GUI to the remote diagnosis server; setting details of a hopping medical diagnosis service; and informing the user of a completion of the sign up.

The details of the hopping medical diagnosis service, such as an interval of mandatory periodic medical consultations (periodic examinations), a limit on the number, of continuous services by the virtual doctor, or a cutoff level, may vary according to a past disease history of the patient, a present disease history of the patient, an opinion of the doctor, sex, age, or disease, and preferably may be determined by the medical expert.

In the initial sign up stage, the details of the hopping medical diagnosis service may be set up as a default value and may vary based on the diagnosis result by the medical expert whenever the remote diagnosis service is terminated.

The interval of mandatory periodic medical consultations (periodic examinations) in the hopping medical diagnosis service may be 6 months, and the limit on the number of continuous services by the virtual doctor may be 10 to 30 times.

The sign up may further include setting up a personal ID and a password.

According to another embodiment of the present invention, there is provided a method of performing a remote medical-diagnosis, the method including:

injecting a sample into a bio-disc or a biochip having a barcode or a RF IC to perform biological, chemical or biochemical reactions;

authenticating a product ID of a bioanalytical device by transmitting the product ID of a bioanalytical device to a remote diagnosis server and registering the authenticated product ID of the bioanalytical device in the remote diagnosis server;

authenticating the bio-disc or the biochip using the bioanalytical device comprising a reader which reads the bar code or the RF IC;

obtaining data by analyzing reaction results obtained by the bio-disc or the biochip using the bioanalytical device;

recording the data and the product ID of the bioanalytical device to the RF IC;

transmitting the data measured by the bioanalytical device to the remote diagnosis server via a communication network;

providing a user with a consulting service by connecting the user with a medical expert during periodic medical consultations and connecting the user with a virtual doctor during non-periodic medical consultations;

blocking the consulting service between the user and the virtual doctor when a periodic medical consultations term has elapsed; and performing a priority connection connecting the user with the medical expert upon receiving a signal requesting for a priority connection even if the periodic medical consultations term has not elapsed.

Even though the bioanalytical device is authenticated via the remote diagnosis server, the bio-disc or the biochip is authenticated by the bioanalytical device including a reader reading the barcode or the RF IC. In this regard, the bio-disc and biochip may be authenticated in a region to which the remote diagnosis server is not connected and efficiently used for a portable bioanalytical device. That is, the bio-disc or the biochip can be authenticated by the bioanalytical device using the reader to read the barcode or the RF IC without employing the remote diagnosis server.

Data measured by the bio-disc or the biochip in a region to which the remote diagnosis server is not connected and the product ID of the bioanalytical device are stored in the RF IC, and the measured data and the product ID stored in the RF IC are transmitted to the remote diagnosis server when the bio-disc or biochip the is loaded on the bioanalytical device connected to the remote diagnosis server.

If the product ID of the bioanalytical device used to measure the data is not registered in the ID registration unit of the remote diagnosis server, the data is determined as invalid by the remote diagnosis server, and the remote diagnosis service cannot be received from the virtual doctor or the medical expert.

There are advantages when the product ID of the bioanalytical device used to measure data is stored in the RF IC, or the product ID of the bioanalytical device stored in the RF IC is transmitted to the remote diagnosis server. First, it can be identified whether the bio-disc and biochip are analyzed using an invalid bioanalytical device or a discarded bioanalytical device, in the remote diagnosis server. That is, medical accidents, which may occur in a remote diagnosis, may be prevented since the bioanalytical device is easily traced and managed. Second, when data of the previously analyzed bio-disc and biochip is obtained only by a cellular phone including the RF IC reader or the RF IC reader without the bioanalytical device, the bioanalytical device that was used to measure the data may be easily detected.

The method may further include: transmitting measured data stored in the RF IC and the product ID of the bioanalytical device used to measure the data to the remote diagnosis server; and detecting whether the product ID of the bioanalytical device is registered in the ID registration unit of the remote diagnosis server when the bio-disc or the biochip is loaded on the bioanalytical device connected to the remote diagnosis server.

The method may further include transmitting cumulative medical data obtained by the virtual doctor before the periodic medical consultation date to the medical expert during the periodic medical consultations.

The present invention also provides a method of performing a remote medical-diagnosis using a remote medical-diagnosis system according to the present invention, the method including: waiting for a checking of whether the bio-disc or the biochip is loaded on the bioanalytical device; automatically or manually activating a GUI on a user's monitor when the bio-disc or the biochip is loaded during the waiting; automatically assaying which sequentially transmits commands for controlling the bioanalytical device to the bioanalytical device; receiving the data measured from the assay site from the hydrogen bonding group after the automatic assaying is completed; and transmitting the measured data to the remote diagnosis server.

The method further includes monitoring blood sampling and injection of the sample by providing guidelines and instructions from the virtual doctor or medical expert about sampling blood and injection of the sample into the bioanalytical device in real time.

The method further includes monitoring serum separation including determining whether serum separation is normally performed by monitoring the state of serum centrifuged or separated using a serum separation device included in the bioanalytical device, and sending a warning message to the user if the serum separation is not normally performed or recording the abnormal serum separation in a history management list.

The method further includes detecting the product ID in order to detect the product ID of the bio-disc, biochip, bioanalytical device, or apparatus for medical examination.

The method further includes upgrading an operational software by downloading a new version of the operational software through the Internet by providing the remote diagnosis server with the product ID when the GUI does not include the operational software corresponding to the product ID of the bioanalytical device and the apparatus for medical examination.

The automatically assaying may include transmitting commands to control a preparation process for preparing a DNA sample obtained from a user; hybridizing the DNA with a capture probe in the assay site; and analyzing the result of the assay site, to the bioanalytical device.

The automatically assaying may further include transmitting commands to control a DNA amplification process amplifying the DNA sample after the preparation process to the bioanalytical device.

The automatically assaying may include transmitting commands to control: a preparation process for preparing serum and antigen from the user; a labeling process forming "label-antigen conjugate" between the label and the antigen; an immune reaction process performing an antigen-antibody conjugate reaction between the "label-antigen conjugate" and a capture probe (immune probe); and a washing process washing and drying the assay site, to the bioanalytical device.

The automatically assaying may include transmitting commands to control: a preparation process for separating serum and antigen from the user; a labeling process forming "label-antigen conjugate" between the label and the antigen; an immune reaction process performing an antigen-antibody conjugate reaction between the antigen and the capture probe (immune probe); and a washing process washing and drying the assay site, to the bioanalytical device.

The automatically assaying may further include transmitting commands to control rotating and stopping the bio-disc; and opening and shutting of a valve of the bioanalytical device.

The method may further include at least one process selected from the group consisting of selecting the medical expert, receiving a check list from the medical expert, transmitting a filled in check list to the medical expert, diagnosing by a medical expert or virtual doctor using an apparatus for medical examination, purchasing medicine according to a medical prescription, transmitting diagnosis results and medical data to a remote diagnosis server, transmitting a history management list of the bioanalytical device to the remote diagnosis server, performing Q & A, and authorizing payment with a card.

The method further includes a medical examination by a virtual doctor requesting the user to correct a misuse of the bioanalytical device and apparatus for medical examination by providing guidelines as how to use the bioanalytical device and apparatus for medical examination or monitoring the use thereof when the virtual doctor is selected from the medical expert selection window.

The method further includes a medical examination by a doctor requesting the user to correct a misuse of the bioanalytical device and apparatus for medical examination by providing guidelines as how to use the bioanalytical device and apparatus for medical examination or monitoring the use thereof when the doctor is selected from the medical expert selection window.

The GUI activates an "assay start" button only when the user signs up on the remote diagnosis server providing a remote diagnosis service, and the user's terminal is connected to the bioanalytical device.

If the user does not sign up on the remote diagnosis server and clicks the "assay start" button, a SMS message or a voice message of "sign up, now" is provided.

The medical examination by a virtual doctor may include at least one process selected from the group consisting of: displaying a mimesis graphic of the user's body on the medical service window in real time by graphically processing images of the user's body, which were taken by a camera using a two-dimensional or three-dimensional animation tool or virtual reality tool; providing the user with guidelines as how to use the apparatus for medical examination step-by-step by sending voice instructions through a speaker; giving instructions to the user as how to use the apparatus for medical examination by superimposing a symbol over a real time mimesis graphic; showing or performing mimesis of the motion of the user on the graphic in real time while monitoring the user using the apparatus for medical examination via the camera; requesting for a correction of a misuse by showing or performing mimesis of the motion of the user on the graphic in real time while monitoring the user using the apparatus for medical examination via the camera; providing positional information on the medical examination by superimposing one symbol illustrating a standard positional information on the apparatus for medical examination over another symbol illustrating a user's positional information on the apparatus for medical examination on the real time mimesis graphic so that the user can recognize the degree of misuse of the apparatus for medical examination; storing data measured by the apparatus for medical examination or transmitting the data to the remote diagnosis server; and informing the user of self-diagnosis results by analyzing the data measured by the apparatus for medical examination using "software for medical examination".

The symbol may be an explanation phrase, an indication line, a cursor, an arrow, a number, and a special symbol, and may blink.

The cameras may be positioned both on the left and right sides of user's terminal or both on the upper and lower sides of user's terminal.

If there is only one camera, information on a perspective view may not be obtained. When the cameras are positioned both on the left and right sides of user's terminal or both on the upper and lower sides of user's terminal, three-dimensional pictures can be obtained, and thus the motion of the user using the apparatus for medical examination can be three-dimensionally monitored. The pictures may be taken using a triangulation method widely known in the art.

The camera may be a visible ray camera, an infrared ray camera, an UV camera, or a fluorescent camera.

In addition, the camera may be a one-dimensional or two-dimensional array camera. The cameras may have different viewing angles.

A special marker may be attached to or painted on at least one portion of the apparatus for medical examination.

The special marker may be easily detected by the camera, and thus be efficiently used in a video tracking, a motion tracking, a capture and standard coordinate set up, recognition of the apparatus for medical examination, and segmentation.

The recognition of the apparatus for medical examination may be conducted by an object recognition, and recognition of a subject and segmentation, as disclosed in a book titled "Digital Image Processing, 2nd edition, Rafael C. Gonzalez and Richard E. Woods, Prentice Hall, 2002".

The special marker may be a light emitting diode (LED) including at least one of a reflective paint, a luminous paint, and a fluorescent paint.

The position and orientation of the apparatus for medical examination may be three-dimensionally identified using the special marker, and the state of the user using the apparatus for medical examination may be tracked or monitored in real time by cumulatively tracking the position of the special marker.

The apparatus for medical examination may be powered by an electromagnetic induction, a solar cell, or a rechargeable battery that may be charged by being connected to a USB port of the user's terminal.

The animation tool is a graphic tool such as OPENGL and 3D Studio MAX and well known in the art.

The software for medical examination includes knowledge and know how of the medical experts in order to diagnose the user by analyzing signals measured by a medical apparatus such as a thermometer, a sphygmomanometer, a stethoscope, a body composition analyzer, an alteriosclerosis detector, an ultrasonic scanning apparatus, an urianalyzer, a pulse monitor, a blood sampling device, an electrocardiogram, an X-Ray apparatus, an oxymeter, a dementia detecting apparatus, a computerized axial tomography (CAT) apparatus, a magnetic resonance imaging (MRI) apparatus, a capsule endoscopy, a magnifier, a magnifier with a camera, a medical instrument, a bio signal detecting apparatus, and a bio shirt having a function of detecting a bio signal (diabetes, obesity, blood pressure, pulse, an electrocardiogram, body temperature, or the like).

The method further includes upgrading an operational software by downloading a new version of the operational software through the Internet when the GUI does not include an operational software including "software for medical examination" and corresponding to a protocol and an assay algorithm of the apparatus for medical examination.

The virtual reality (VR) tool may further include a virtual reality (VR) cap and virtual reality (VR) gloves to provide the user's terminal or the medical expert with information on a three-dimensional position of the user, information on the orientation, or three-dimensional information on the use of the apparatus for medical examination.

The VR tool may further include a pair of virtual reality (VR) glasses to provide a virtual reality (VR) doctor.

The pair of VR glasses provides the user with a visual image of the VR doctor who gives guidelines as the how to use the apparatus for medical examination as if the VR doctor or the medical expert is standing beside the user and giving instructions.

The communication between the user and the virtual doctor or medical expert may be facilitated by receiving the guidelines or instructions from the virtual doctor or medical expert through the pair of VR glasses.

The pair of VR glasses, the VR cap, the VR gloves, the apparatus for medical examination, and the bioanalytical device may be connected to the user's terminal in a wired or wireless manner.

The wireless connection may be conducted by an infrared communication, a Bluetooth communication, or a RF communication.

In the method of performing a remote medical-diagnosis according to the present invention, the medical examination by the medical expert includes: transmitting images of the user, which were taken by a camera, to the medical expert or displaying the images on a medical service window in real time; providing the user with guidelines as how to use the apparatus for medical examination step-by-step by sending voice instructions through a speaker; giving instructions to the user as how to use the apparatus for medical examination by superimposing a cursor, an arrow, or an indication line provided by the medical expert on the medical service window; requesting for a correction of a misuse while the user using the apparatus for medical examination is monitored by the medical expert via a camera; storing data measured by the apparatus for medical examination or transmitting the data to the remote diagnosis server and the medical expert; and informing the user of diagnosis results obtained by the medical expert by analyzing data measured by the apparatus for medical examination.

In the method, the medical examination by the user includes: recording the state of the user using the apparatus for medical examination by using a camera; transmitting data measured by the apparatus for medical examination and the recorded data to a remote diagnosis server and a doctor; and informing the user of diagnosis results obtained by the doctor by analyzing the measured data and recorded data via a message transmittance means.

The medical examination by the virtual doctor, the medical expert, or the user further includes at least one of: requesting the user to be aligned with the camera; tracking the camera in which the user is framed, and a focus and magnification of the camera are automatically controlled in real time, remotely controlled by the medical expert, or controlled when the user clicks a "camera environment set up" button; and selecting the apparatus for medical examination by an "apparatus selection" button.

In the tracking of the camera, the alignment of the camera may be conducted in a two-dimensional or three-dimensional space by forward and reverse rotations of a step motor connected to the camera and engaged with a gear.

The automatic control of the focus and magnification of the camera is well known in the art.

Hereinafter, the present invention will now be described more fully with reference to the accompanying drawings, in which exemplary embodiments of the invention are shown. Like reference numerals in the drawings denote like elements.

FIG. 1 shows a block diagram of a remote medical-diagnosis system that uses the Internet, according to an embodiment of the present invention Referring to FIG. 1, the remote medical-diagnosis system according to the present embodiment of the present invention includes a remote diagnosis server 30a providing a remote diagnosis service, a plurality of user's terminals 10a connected to each other through an Internet network 20 and communicating with each other via the remote diagnosis server 30a, and a plurality of medical expert's terminals 10b.

The remote diagnosis server 30a connects the user's terminals 10a requesting for a remote diagnosis service through the Internet network 20 with the medical expert's terminals 10b providing the remote diagnosis service in real time. The remote diagnosis server 30a is connected to: a users DB 50a, a medical expert DB 50b, and a charging DB 50c; a history DB 50d storing a diagnosis history and a history management list; a charging server 30b, a medical insurance server 40a, a card company server 40b, a bank server 40c, and a pharmacy server 40d in order to charge the user for the remote diagnosis service and medicine, and complete the payment; and a wireless communication server 40e which wirelessly transmits the charges list and the remote diagnosis list to the user or connects a wireless terminal of the user such as a cellular phone or a wireless PDA with the medical expert's terminal 10b in a wireless manner.

In order for a medical expert to provide the remote diagnosis service via the remote diagnosis server 30a using the medical expert's terminal 10b, the medical expert accesses the remote diagnosis server 30a using the medical expert's terminal 10b and signs up or registers on the remote diagnosis server 30a. For the sign up or registration, information on ID, password, name, age, occupation, specialty, company, picture, education, work experience, qualification, or the like of the medical expert is required. By the sign up or registration, information on the medical expert is stored in and managed by the medical experts DB 50b of the remote diagnosis server 30a. When the medical expert accesses the remote diagnosis server 30a via the medical expert's terminal 10b, the remote diagnosis server 30a authenticates the medical expert using the medical experts DB 50b and creates a medical consultation window for the medical expert to therewith provide the user with a remote diagnosis service in real time.

In order for the user to receive the remote diagnosis service via the remote diagnosis server 30a using the user's terminal 10a, the user also accesses the remote diagnosis server 30a using the user's terminal 10a, and signs up or registers on the remote diagnosis server 30a by any one of the two methods below.

Firstly, for the sign up or registration, information on ID, password, name, nationality, e-mail, occupation, specialty, address, telephone number, cellular phone number, date of birth, sex, past disease history, family disease history, etc., of the user is required. By the sign up or registration, information on the user is stored in and managed by the users DB 50a of the remote diagnosis server 30a.

In addition, for the sign up or registration of the user, bank name, account holder, account number, credit card number, or the like are further required, and the information is stored in and managed by the charge DB 50c.

Secondly, when a card is inserted into a card reader 99, the remote diagnosis server 30a receives personal information read from the card reader 99, and the personal information is stored in and managed by the users DB 50a. In this regard, if the card is a check card or a debit card, the remote diagnosis server 30a inquires a bank server 40c for the validity of the check card, and if the card is a credit card, the remote diagnosis server 30a inquires a card company server 40b for the validity of the credit card. If the card is a medical insurance card, the remote diagnosis server 30a inquires a medical insurance server 40a for the validity of the medical insurance card. Then, the user gets a personal ID and a password.

In addition, when the user is registered, information on the card is stored in and managed by the charge DB 50c.

The card reader 99 may be embedded in a rim around a screen of a monitor of each of the user's terminals 10a. When the user accesses the remote diagnosis server 30a via the user's terminal 10a, the remote diagnosis server 30a authenticates the user using the users DB 50a, and the user selects one of the medical experts provided by the remote diagnosis server 30a to receive a remote diagnosis service or medical consultation service from the medical expert.

The charging DB 50c monitors a duration of time during which the user's terminal 10a and the medical expert's terminal 10b access the remote diagnosis server 30a and receive the remote diagnosis service, and transmits a charges list prepared based on the duration of time and fees for the remote diagnosis service predetermined by the medical expert to the user's terminal 10a. When the user accepts the charges list, the charging DB 50c requests the related medical insurance server 40a, the bank server 40c, the card company server 40b, etc., for authorization of the payment in order to complete the payment.

The payment may be completed by inserting the card into the card reader 99 or by electronic money.

The user's terminals 10a are wired or wireless IT information terminals such as computers capable of duplex communications by being connected with each other via the Internet network 20. The user's terminals 10a access the remote diagnosis server 30a to receive the remote diagnosis service from the medical expert's terminals 10b via a communication network. The user's terminals 10a may each include a camera 15, a headset or a microphone 14, etc., for a video chat, a voice chat, and a text chat.

The medical expert's terminals 10b are wired or wireless IT information terminals such as computers capable of duplex communications by being connected with each other via the Internet network. The medical expert's terminals 10b accesses the remote diagnosis server 30a to provide the remote diagnosis service requested by the user's terminals 10a via a communication network. The medical expert's terminal 10b, like the user's terminal 10a, may each include a camera 15, a headset or a microphone 14, etc., for a video chat, a voice chat, and a text chat. The user's terminals 10a may also each include a mouse 11, a bioanalytical device 100, and an apparatus 101 for medical examination.

The user may receive a medical diagnosis using the bioanalytical device 100 and the apparatus 101 for medical examination according to the following three methods.

In a first method, the user receives a medical diagnosis from a doctor from the beginning to the end. That is, the user requests for a remote diagnosis service, obtains data from the bioanalytical device 100 and the apparatus 101 for medical examination according to instructions of the doctor, and requests the doctor for a diagnosis based on the measured data.

In a second method, the user obtains data from the bioanalytical device 100 and the apparatus 101 for medical examination according to instructions of a virtual doctor provided by a GUI, and requests a doctor for a remote diagnosis service based on the measured data.

In a third method, the user receives a medical diagnosis from a virtual doctor from the beginning to the end. That is, the user obtains data from the bioanalytical device 100 and the apparatus 101 for medical examination according to instructions of a virtual doctor provided by a GUI, and requests the virtual doctor for a diagnosis based on the measured data.

The first method is advantageous for users who are not aware of how to use the bioanalytical device 100 and the apparatus 101 for medical examination, but the fees for the service are expensive. On the other hand, the third method may cause a misdiagnosis even though the fees for the service are inexpensive.

Thus, in order to reduce the costs for the remote diagnosis service and a chance of the misdiagnosis, a following method in which these three methods are mixed may be used, according to an embodiment of the present invention.

That is, the present invention provides a remote medical-diagnosis system and a method thereof in which the user mandatorily receives a remote diagnosis service periodically (for example, once a month) using the first or second diagnosis method, and receives a remote diagnosis service using the third diagnosis method for a period except for the periodical diagnosis, that is, the user obtains data from the bioanalytical device 100 and the apparatus 101 for medical examination according to instructions of a virtual doctor provided by a GUI, and the virtual doctor informs the user of the diagnosis results based on the measured data.

In addition, the present invention also provides a remote medical-diagnosis system and a method thereof in which the user receives a medical service using the first method even if the medical service is not the periodic medical consultation, if requested by the user, if abnormal conditions are detected by the virtual doctor, and if the diagnosis service with the virtual doctor is performed over a predetermined number of times, or after a predetermined period of time (e.g., 6 months) since the patient receives the last remote diagnosis service from the doctor.

The mixed medical service will be referred to as a "hopping medical diagnosis service".

The present invention provides a method of performing a remote medical-diagnosis using a hopping medical diagnosis service including periodic medical consultations for receiving a remote diagnosis service from the doctor and non-periodic medical consultations for receiving a medical diagnosis service from the virtual doctor by combining the periodic medical consultations in which the user obtains data from the bioanalytical device 100 and the apparatus 101 for medical examination according to instructions of the remote medical expert and requests the medical expert for a diagnosis based on the measured data, and the non-periodic medical consultations in which the user obtains data from the bioanalytical device 100 and the apparatus 101 for medical examination according to instructions of the virtual doctor and requests the virtual doctor for a diagnosis service based on the measured data for a period except for the periodical diagnosis.

According to the hopping medical diagnosis service, if a periodic medical consultations is not conducted or a periodic medical consultations term has elapsed, a GUI for the non-periodic medical consultations may not be activated or the non-periodic medical consultations cannot be conducted.

That is, the patient should receive the periodic medical consultations from the doctor to receive the non-periodic medical consultations from the virtual doctor.

The virtual doctor provides a self-diagnosis method such as a breast cancer self-examination, a prostatitis self-examination, and melancholia self-examination.

Referring to FIG. 1, a method of performing a remote diagnosis service in which the user accesses the remote diagnosis server 30a using the user's terminal 10a and receives the remote diagnosis service from the medical expert using the remote medical-diagnosis system according to the present invention will be described.

In this regard, it is assumed that the medical expert accesses the remote diagnosis server 30a via the medical expert's terminal 10b, is authenticated by the remote diagnosis server 30a based on the medical expert information stored in the medical experts DB 50b, and opens a medical consultation window providing a remote diagnosis service before the user requests for the remote diagnosis service.

First, when the user accesses the remote diagnosis server 30a via the user's terminal 10a, the remote diagnosis server 30a requests a personal ID and a password of the user. When the user inputs the personal ID and the password or inserts a card into the card reader 99, the remote diagnosis server 30a confirms the user's registration based on the user information stored in the users DB 50a and authenticates the user.

After the user is authenticated, the remote diagnosis server 30a displays current medical experts by opening a medical consultation window to the user, and then the user selects one of the medical experts.

If the selected medical expert is not the virtual doctor, the remote diagnosis server 30a operates the medical consultation window in the user's terminal 10a, and connects the user's terminal 10a requesting for the remote diagnosis service with the medical expert's terminal 10b corresponding to the selected medical expert so as to provide a remote diagnosis service via the Internet in real time.

On the other hand, if the selected medical expert is the virtual doctor, the virtual doctor provides the remote diagnosis service via a GUI.

According to the present invention, during the periodic medical consultations, the medical expert can only be selected, and a diagnosis service cannot be received from the virtual doctor.

When the remote diagnosis service is terminated, the user's terminal 10a and the medical expert's terminal 10b terminate their respective medical consultation windows, and the remote diagnosis server 30a checks a start-time and a finish-time of the remote diagnosis service, i.e., a service time so that the data is stored in and managed by the remote diagnosis service.

The remote diagnosis server 30a transmits the charges list to the user's terminal 10a based on the service time stored in the charging DB 50b and the standard fees for the service set by the medical expert, and requests the related medical insurance server 40*a*, the card company server 40*b*, and the bank server 40*c* for authorization of the payment in order to complete the payment if the user accepts the charges list.

Figure 2:
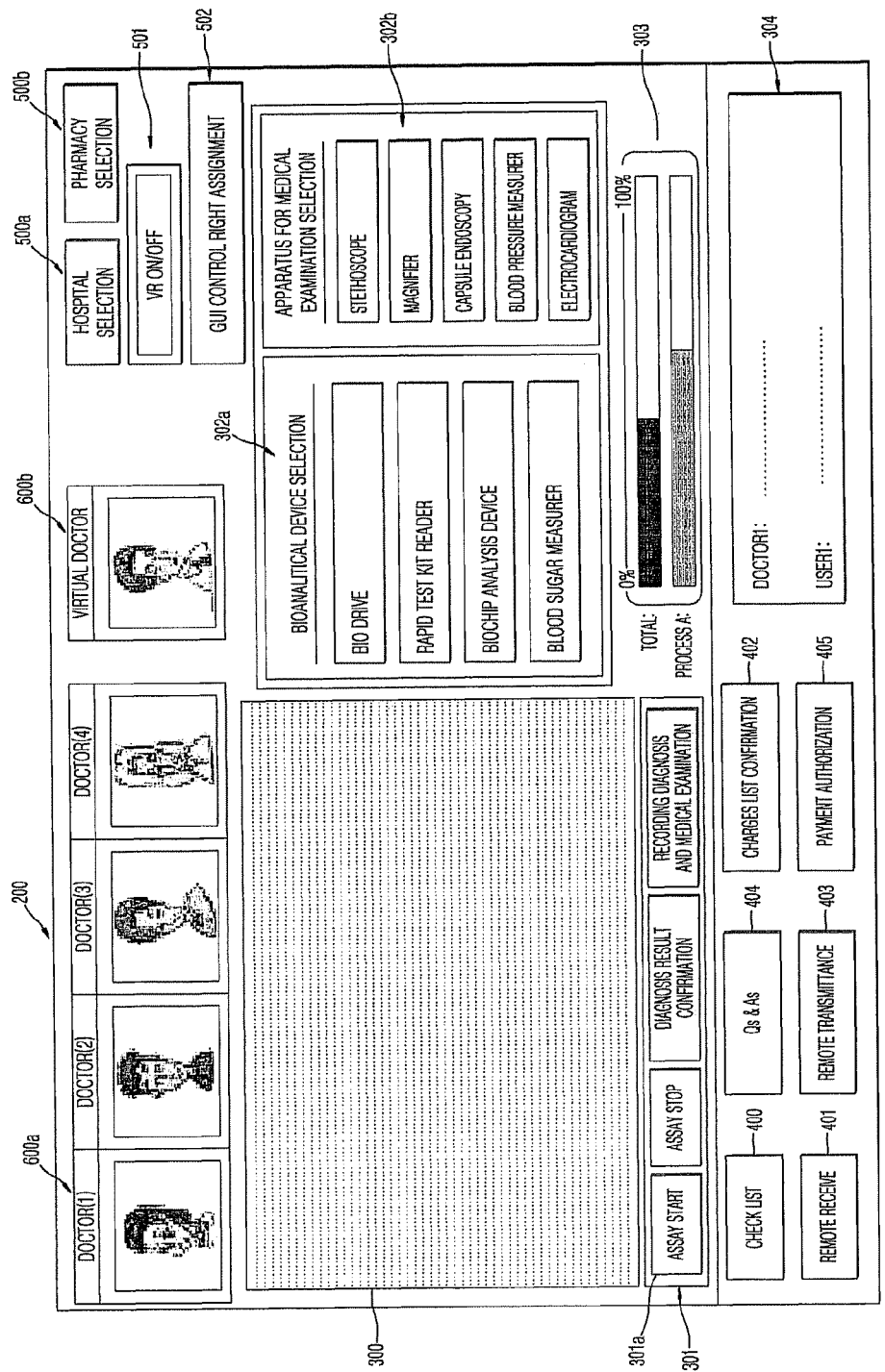
FIG. 2 shows a graphic user interface (GUI) of a remote medical-diagnosis system, according to an embodiment of the present invention.

FIG. 2 shows a GUI 200 of the remote medical-diagnosis system, according to an embodiment of the present invention.

Referring to FIG. 2, the GUI 200 includes a variety of buttons and windows in order to provide the user with convenient access to the remote medical-diagnosis system.

The GUI 200 includes a button panel 301 including function buttons, and a window 303 displaying a rate of progress of the bioanalytical device 100.

The GUI 200 also includes a panel 302*a* on which buttons for selecting the bioanalytical device 100 are arranged, and a panel 302*b* on which buttons for selecting the apparatus 101 for medical examination are arranged. In addition, the GUI 200 includes a chat window 304 for a text chat.

The GUI 200 monitors the state of operation and progress of the bioanalytical device 100 connected to the user's terminal 10*a* using a wired or wireless communication means between the user's terminal 10*a* and the bioanalytical device 100 in real time, or controls operation of the bioanalytical device 100 by sending a control command to the bioanalytical device 100. That is, the GUI 200 confirms whether the user's terminal 10*a* is connected with the bioanalytical device 100 and whether the bio-disc or the biochip is loaded on the bioanalytical device 100. If an "assay start" button 301*a* is clicked, the GUI 200 sequentially transmits commands for controlling the bioanalytical device 100 to the bioanalytical device 100 according to predetermined protocols. In addition, the GUI 200 receives data measured from the bioanalytical device 100 after the bioanalytical device 100 finishes the assay.

The GUI 200 further includes a medical service window 300 to display data measured by the bioanalytical device 100 in terms of numbers, in a graph, or a high-medium-low form, display data measured by the apparatus 101 for medical examination in terms of numbers, in a graph, or a high-medium-low form, display diagnosis results obtained from the bioanalytical device 100 and the apparatus 101 for medical examination, display a check list or Qs & As, display a mimesis of the user's body using the bioanalytical device 100 and the apparatus 101 for medical examination in real time, display how to use the bioanalytical device 100 and the apparatus 101 for medical examination provided by the medical expert, display a charges list, display a medical prescription received from the medical expert, provide a window displaying a DVD film, a TV program, a DMB broadcast, or a multimedia program, provide a window for Internet surfing or computer applications, display ten keys and a video image of a counterpart for telephone communication, input information related to the remote diagnosis service and the GUI and notify the user of an additional text message, or display the content of the text message.

In addition, the GUI 200 includes: a "remote transmittance" button 403 to store data measured by the bioanalytical device 100, a check list, Qs & As, information on the details of the remote diagnosis during a remote diagnosis, or medical data in the remote diagnosis server 30*a* or transmits them to the medical expert; a "remote receiving" button 401 to receive diagnosis results, a medical prescription, a check list, Qs & As, medical data, or a charges list from the medical expert or the remote diagnosis server 30*a*; a "charges list admission" button 402 to accept the charges list; a "payment authorization" button 405 to authorize payment of fees for the remote diagnosis service using electronic money, a card, or a cellular phone; a "check list" button 400 to edit or examine the check list; a "Qs & As" button 404 to write or examine the Qs & As; a "VR ON/OFF" button 501 to set up a virtual reality remote diagnosis mode using the virtual reality tools; medical expert selection buttons 600*a* and 600*b* to select a medical expert; a hospital selection button 500*a* and pharmacy selection button 500*b* to respectively select the hospital and the pharmacy; and a "control assignment" button 502 to assign the "remote control right" of the GUI to the selected medical expert.

If the "remote control right" of the GUI is assigned to the selected medical expert, the medical expert can remotely control the GUI 200 of the user's terminal 10*a*. Thus, the user may easily receive a remote diagnosis service from the medical expert by using the bioanalytical device 100 and the apparatus 101 for medical examination even if the user is not aware of how to use the GUI 200. Even though the remote control right is assigned to the medical expert, the "payment authorization" right still belongs to the user.

FIGS. 3 to 6 show examples of the GUI 200 providing a remote diagnosis service according to different devices selected as the apparatus 101 for medical examination.

Figure 3:
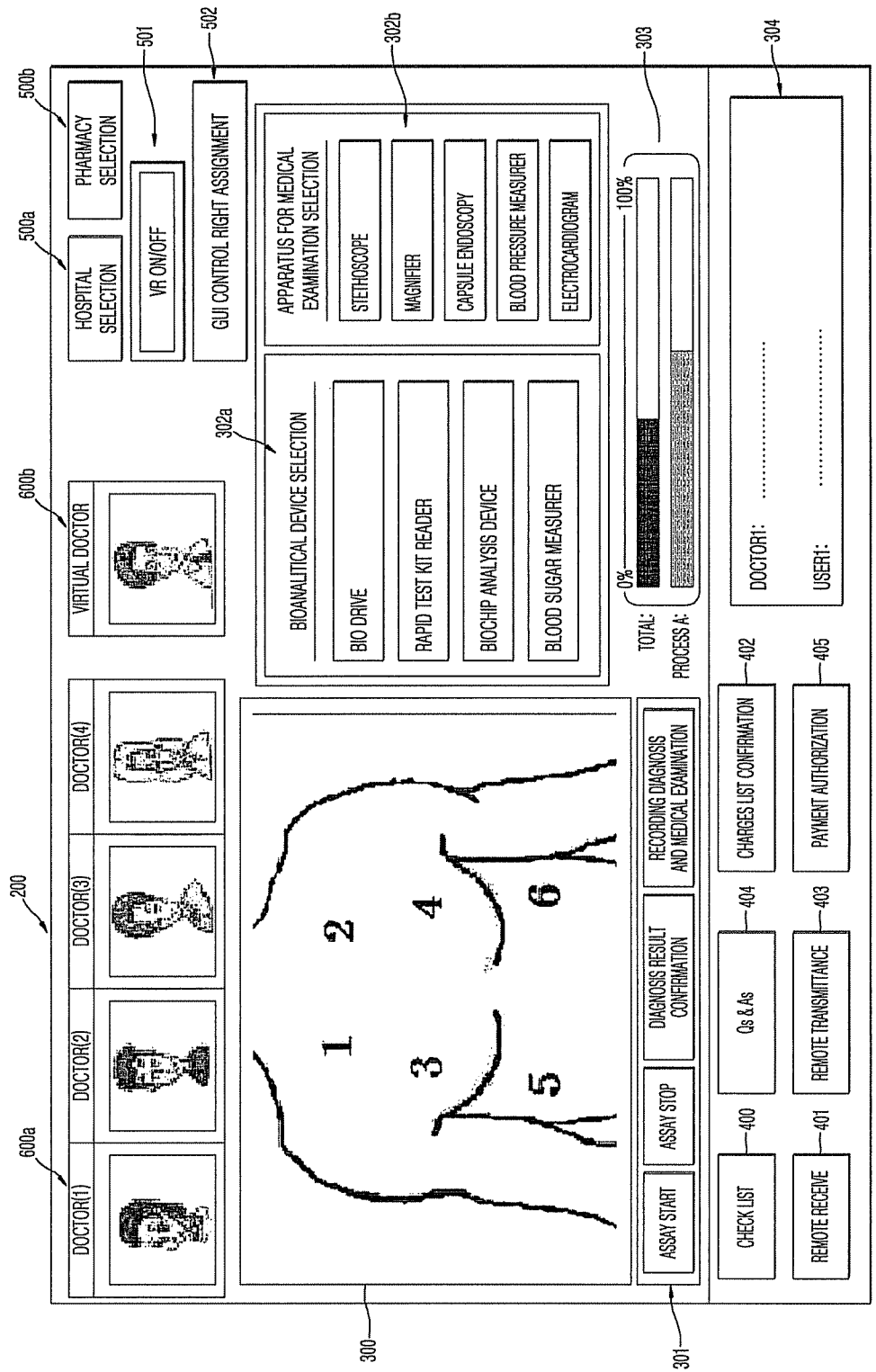
FIG. 3 shows the GUI of a remote medical-diagnosis system when a user receives a remote diagnosis service by selecting a stethoscope as an apparatus for medical examination.

FIG. 3 shows the GUI 200 of a remote medical-diagnosis system when a user receives a remote diagnosis service by selecting a stethoscope as the apparatus 101 for medical examination.

For example, instructions as how to use the apparatus 101 for medical examination may be given to the user 1) using a medical service window 300 by obtaining a video image of the user's body using the camera 15 and superimposing a symbol over the video image of the user's body with regard to a standard diagnostic position to place a stethoscope, 2) using the medical service window 300 by superimposing a symbol over a real time mimesis graphic with regard to a standard diagnostic position to place a stethoscope, or 3) using the medical service window 300 by obtaining a video image of the user's body using the camera 15 and superimposing a symbol received by the remote doctor in real time over the video image of the user's body with regard to a standard diagnostic position to place a stethoscope.

The symbol may be an explanation phrase, an indication line, a cursor, an arrow, a number, and a special symbol, and may blink. In FIG. 3, the position and the order of the standard medical examination were displayed on the medical service window 300 using numbers 1, 2, 3, 4, 5 and 6.

The GUI 200 may provide the user with both the video image and the voice explanation such that a voice explanation is synchronized with the animation image (mimesis graphic) or a voice explanation is received from the doctor in real time while instructions for the method of using the apparatus 101 for medical examination are provided to the user via the medical service window 300.

The medical service window 300 of the GUI 200 may also be provided to the doctor via the medical expert's terminal 10*b* in real time.

Figure 4:
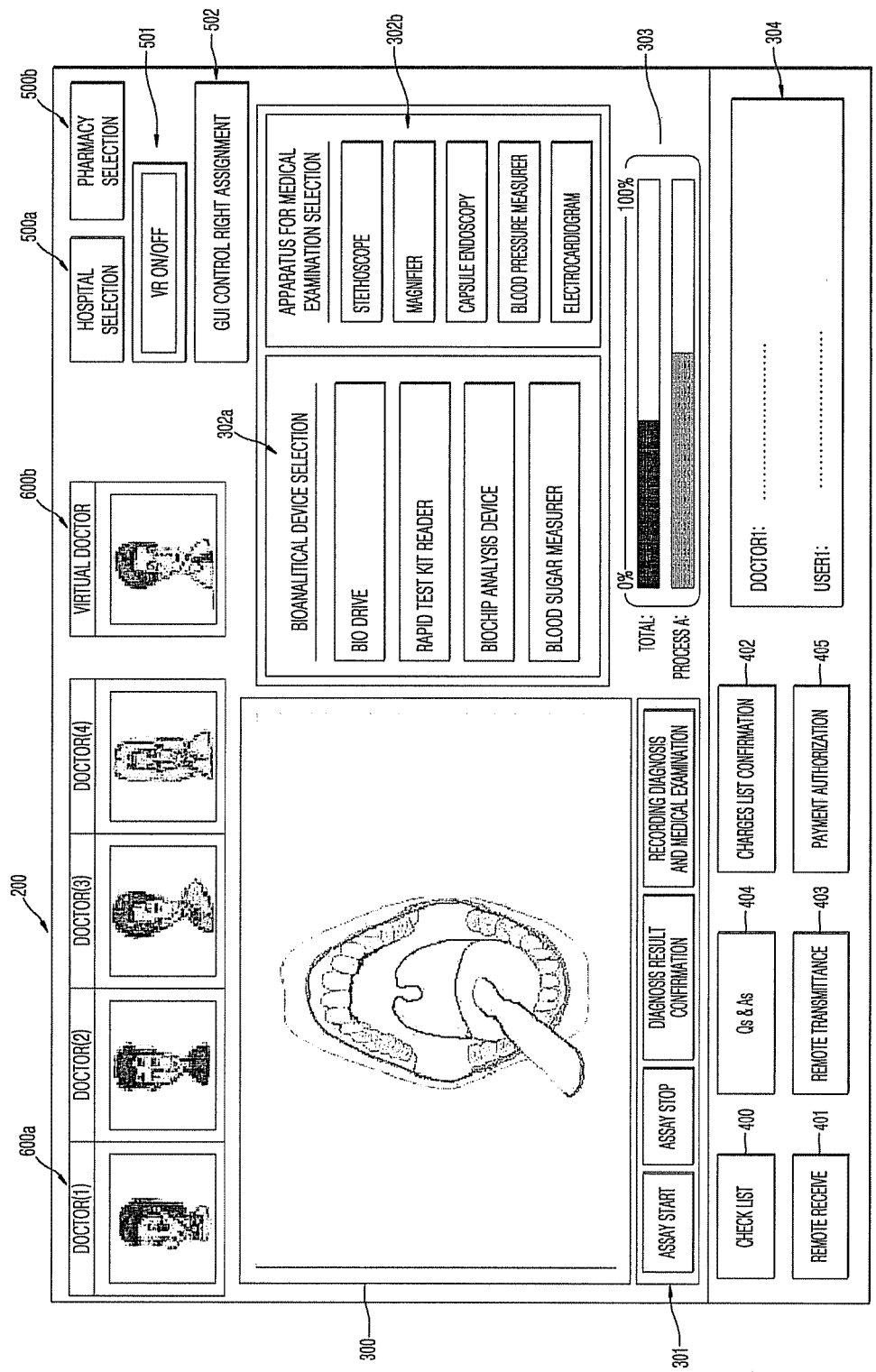
FIG. 4 shows the GUI of a remote medical-diagnosis system when a user receives a remote diagnosis service by selecting a camera-integrated magnifier as the apparatus for medical examination.

FIG. 4 shows the GUI 200 of a remote medical-diagnosis system when a user receives a remote diagnosis service by selecting a camera-integrated magnifier as the apparatus 101 for medical examination. Referring to FIG. 4, the medical service window 300 displays the inside of the mouth of the user using a magnifier.

Figure 5:
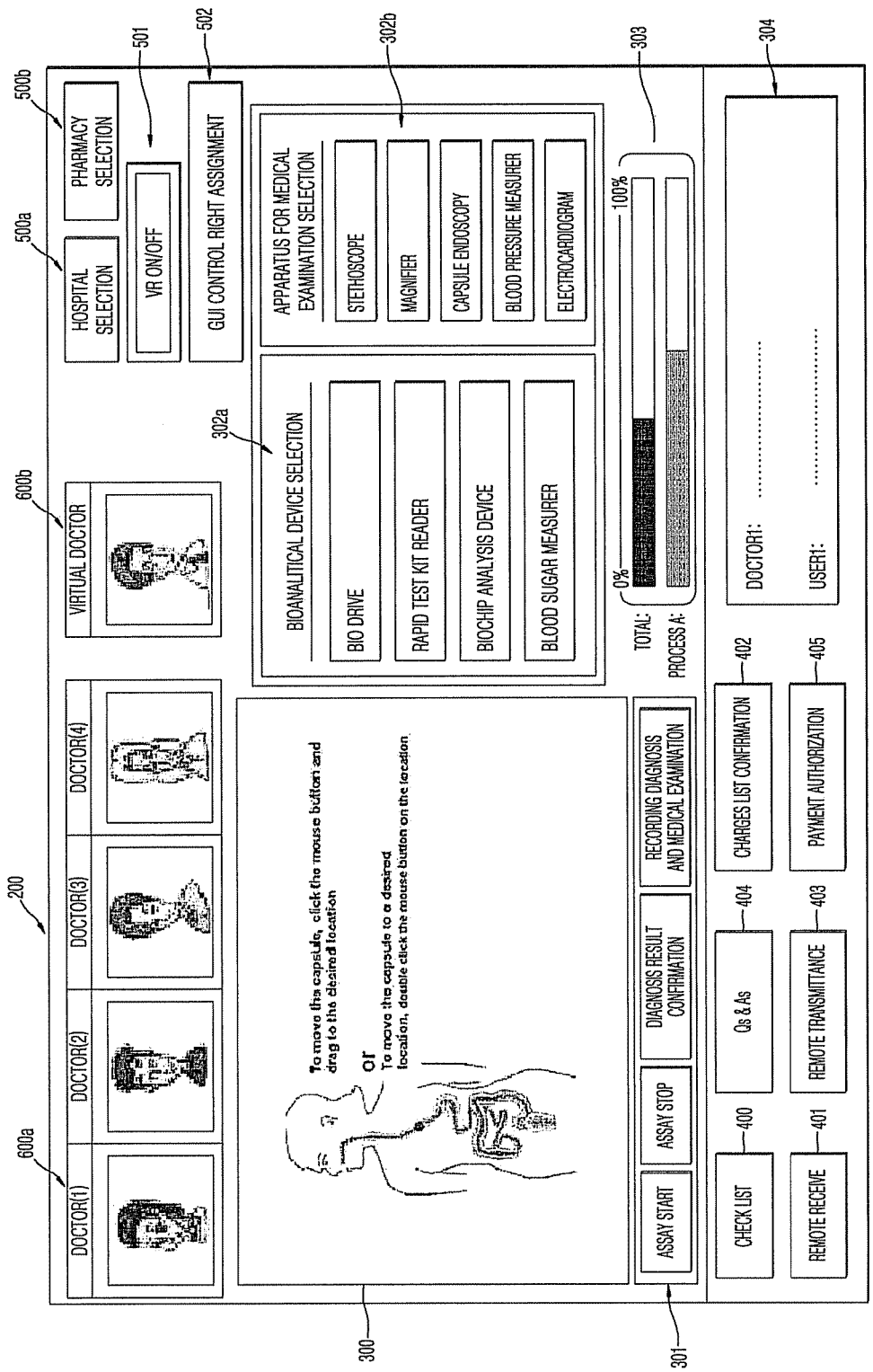
FIG. 5 shows the GUI of a remote medical-diagnosis system when a user receives a remote diagnosis service by selecting a capsule endoscopy as the apparatus for medical examination.

FIG. 5 shows the GUI 200 of a remote medical-diagnosis system when a user receives a remote diagnosis service by selecting a capsule endoscopy as the apparatus 101 for medical examination. Referring to FIG. 5, both the inside of the user's body and a current position of a capsule endoscopy 72 are displayed on the medical service window 300. The images of the inside of the body, which are taken by the capsule endoscopy 72 moving around the inside the body, are transmitted to the user's terminal 10a using a wireless communication means, and observed by the doctor in real time.

Figure 6:
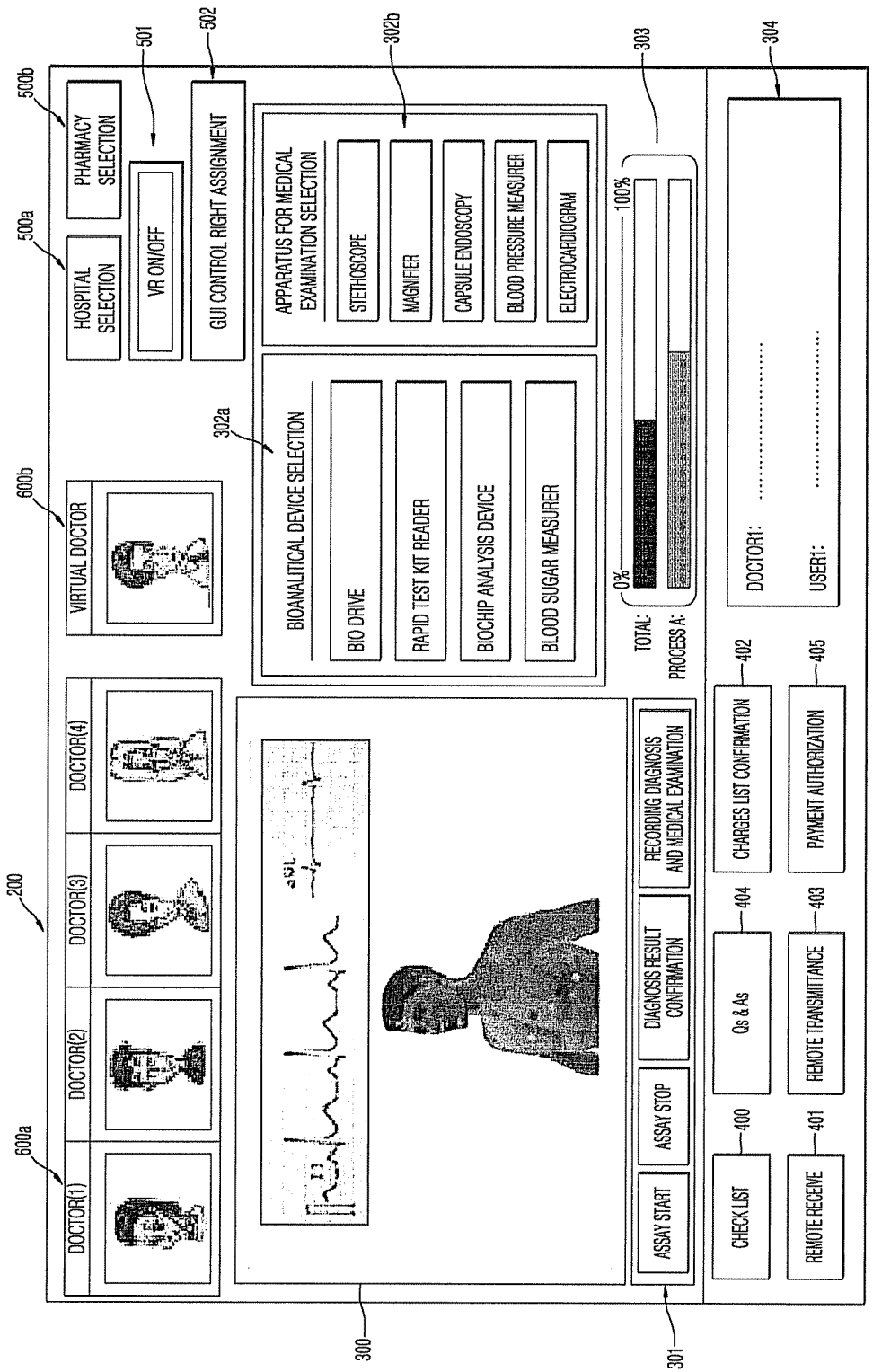
FIG. 6 shows the GUI of a remote medical-diagnosis system when a user receives a remote diagnosis service by selecting an electrocardiogram as the apparatus for medical examination.

FIG. 6 shows the GUI 200 of a remote medical-diagnosis system when a user receives a remote diagnosis service by selecting an electrocardiogram as the apparatus 101 for medical examination. Referring to FIG. 6, a standard diagnostic position of the electrocardiogram and a current position of the electrocardiogram are displayed on the medical service window 300.

FIGS. 7 to 10 show examples of the GUI 200 providing a remote diagnosis service according different devices selected as the bioanalytical device 100.

Figure 7:
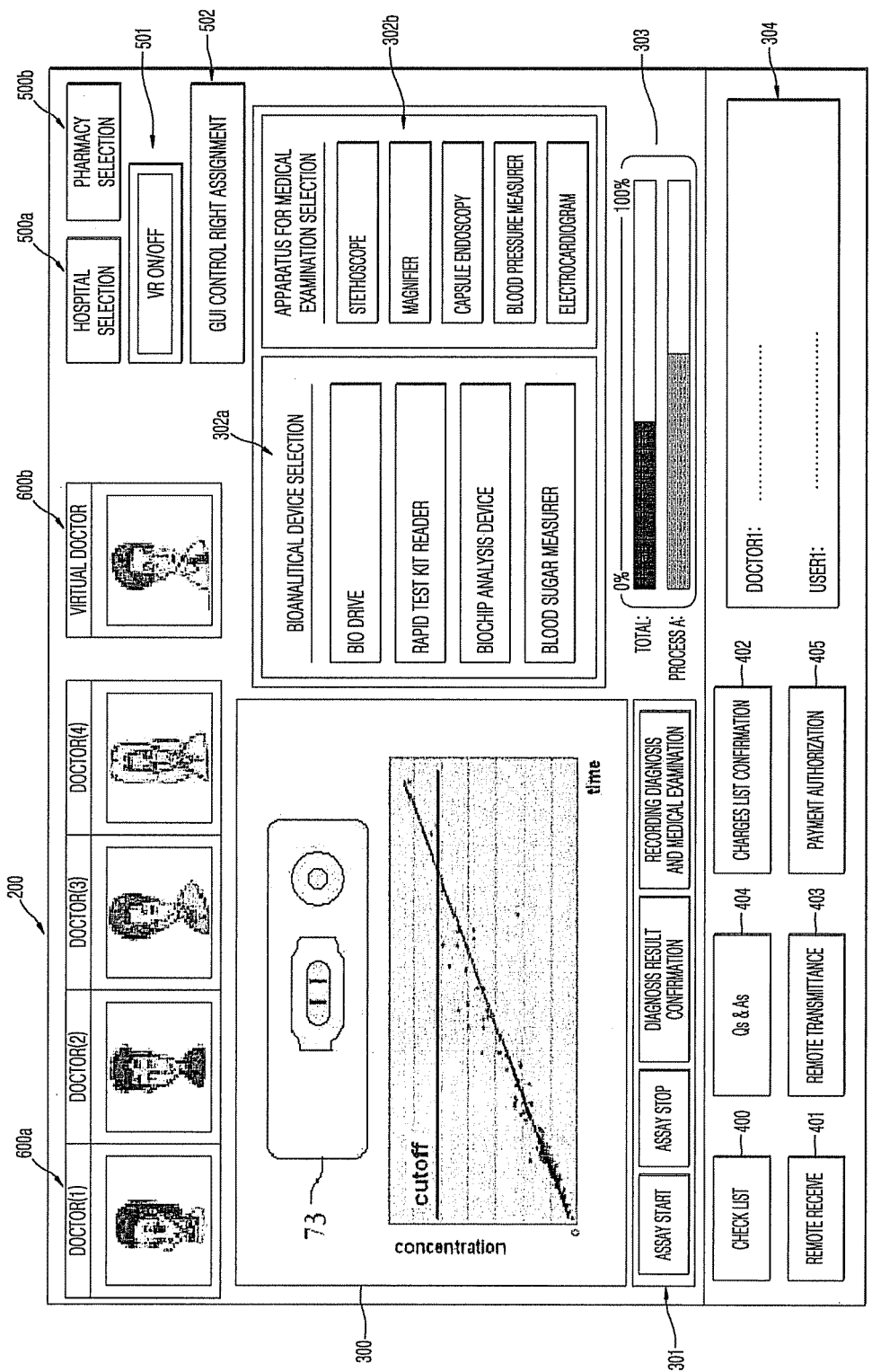
FIG. 7 shows the GUI of a remote medical-diagnosis system when a user receives a remote diagnosis service by selecting a Rapid Test Kit Reader as a bioanalytical device.

FIG. 7 shows the GUI 200 of a remote medical-diagnosis system when a user receives a remote diagnosis service by selecting a Rapid Test Kit Reader as the bioanalytical device 100. Referring to FIG. 7, data measured by the Rapid test Kit 73 and cumulative data previously obtained are displayed on the medical service window 300 using a graph with a cutoff level. The cumulative data previously obtained significantly contributes to early detection of a disease and a reduction in the misdiagnosis rate since a disease can be traced and tracked.

Figure 8:
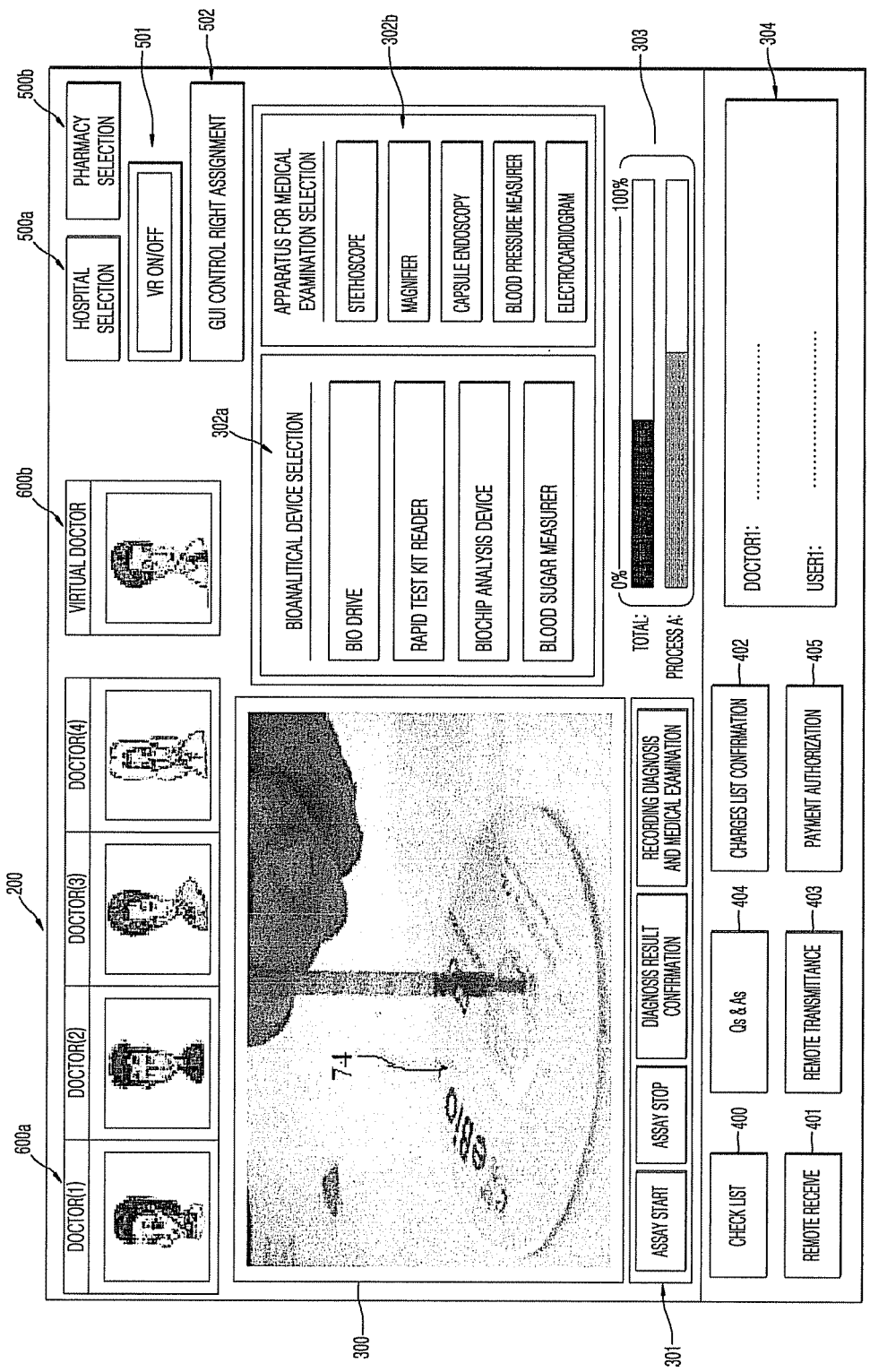
FIG. 8 shows the GUI of a remote medical-diagnosis system displaying the process of injecting blood into a bio-disc to a remote medical expert in real time when a user receives a remote diagnosis service by selecting a bio drive as the bioanalytical device.
Figure 9:
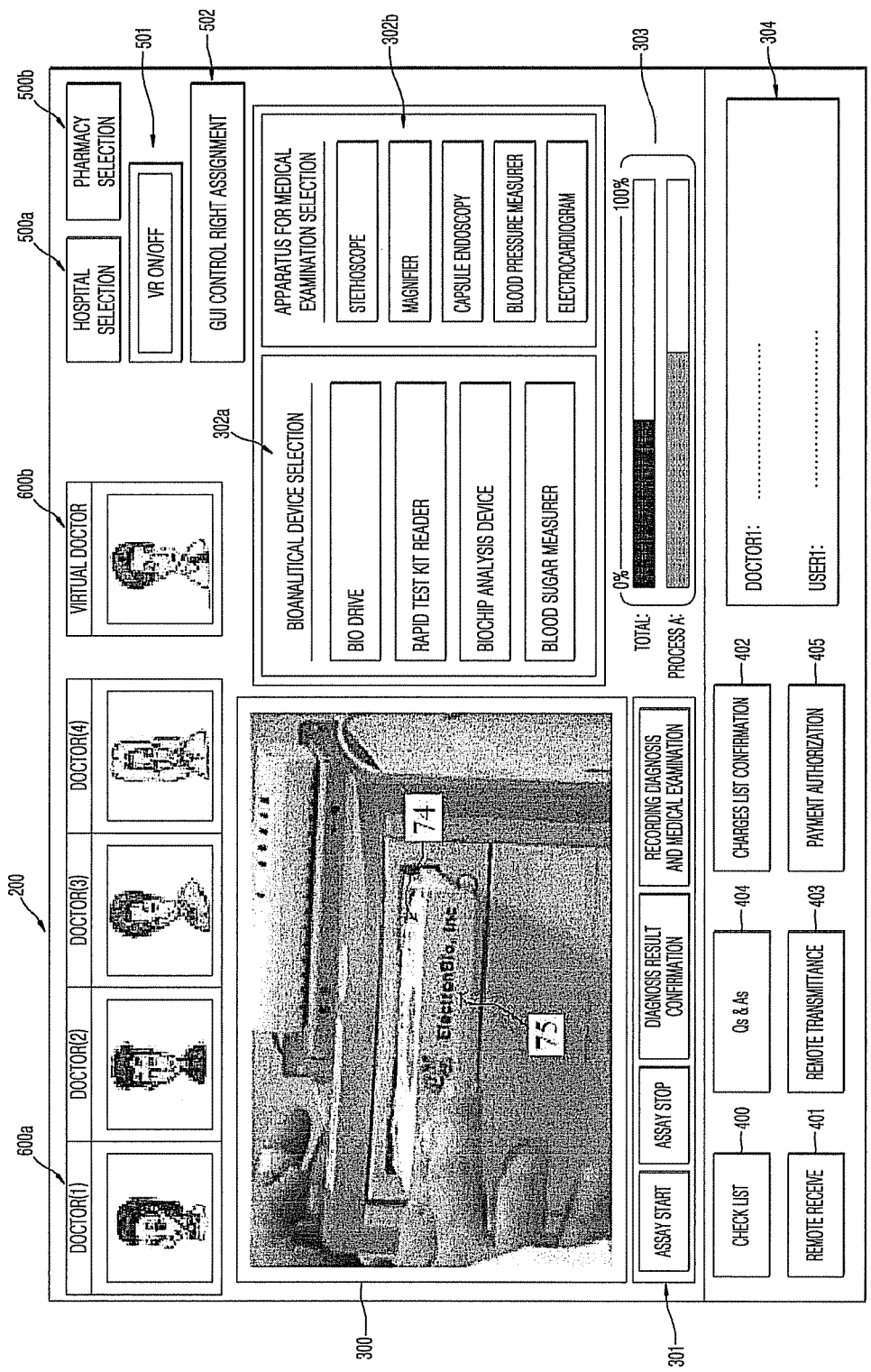
FIG. 9 shows the GUI of a remote medical-diagnosis system displaying the process of loading a bio-disc on a bio drive to a remote medical expert in real time when a user receives a remote diagnosis service by selecting a bio drive as the bioanalytical device.
Figure 10:
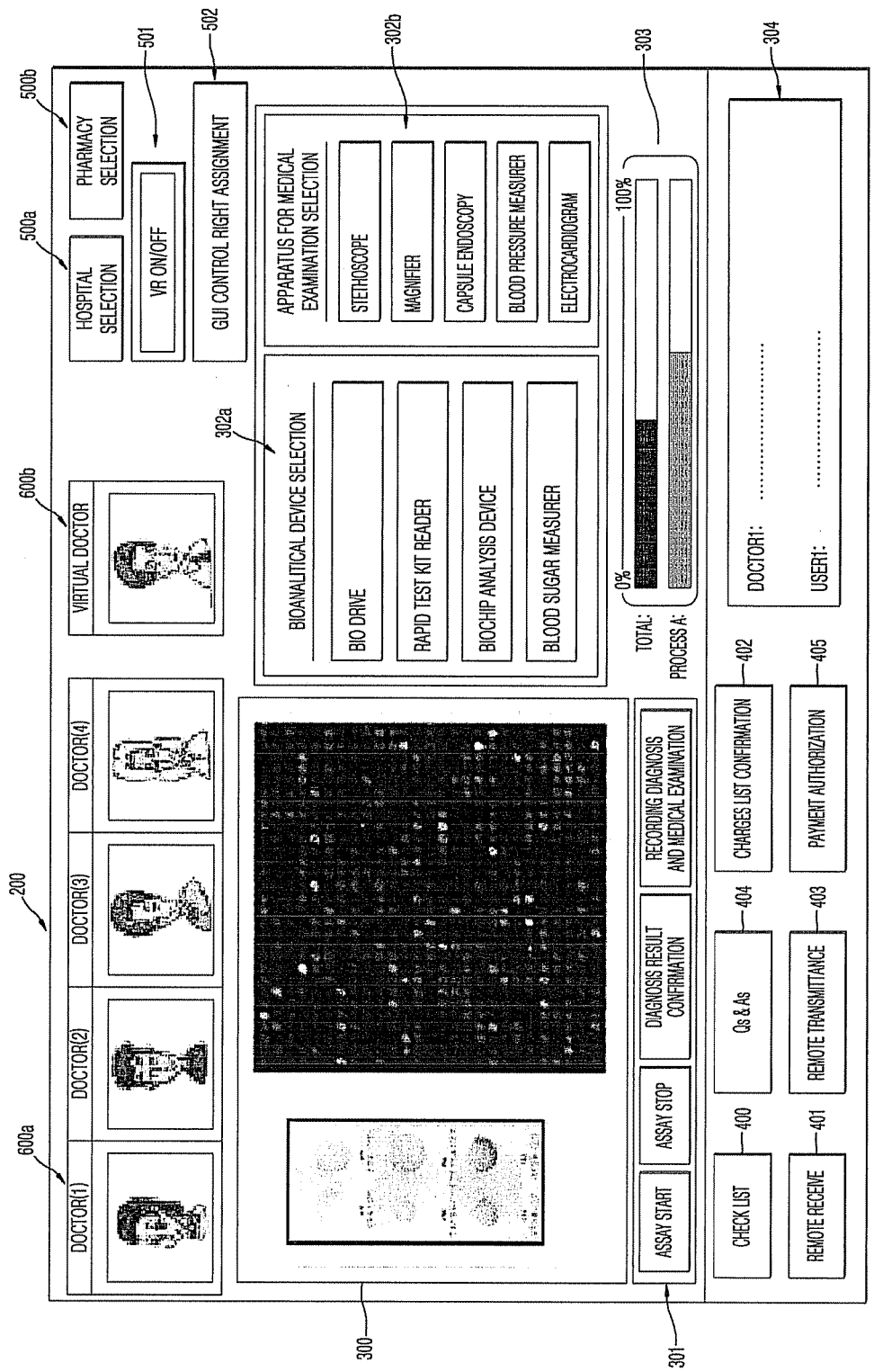
FIG. 10 shows the GUI of a remote medical-diagnosis system displaying data obtained using the bioanalytical device on a medical service display to a user and a remote medical expert in real time when a user receives a remote diagnosis service by selecting a bio drive as the bioanalytical device.

FIGS. 8 to 10 show examples of the GUI 200 providing a remote diagnosis service by selecting the bio drive as the bioanalytical device 100.

FIG. 8 shows the GUI 200 of a remote medical-diagnosis system displaying the process of injecting blood into a bio-disc to a remote medical expert in real time when a user receives a remote diagnosis service by selecting a bio drive as the bioanalytical device 100.

FIG. 9 shows the GUI 200 of a remote medical-diagnosis system displaying the process of loading a bio-disc on a bio drive to a remote medical expert in real time when a user receives a remote diagnosis service by selecting a bio drive as the bioanalytical device 100.

FIG. 10 shows the GUI 200 of a remote medical-diagnosis system displaying data, obtained using the bioanalytical device 100, on a medical service display to a user and a remote medical expert in real time when a user receives a remote diagnosis service by selecting a bio drive as the bioanalytical device 100.

Figure 11:
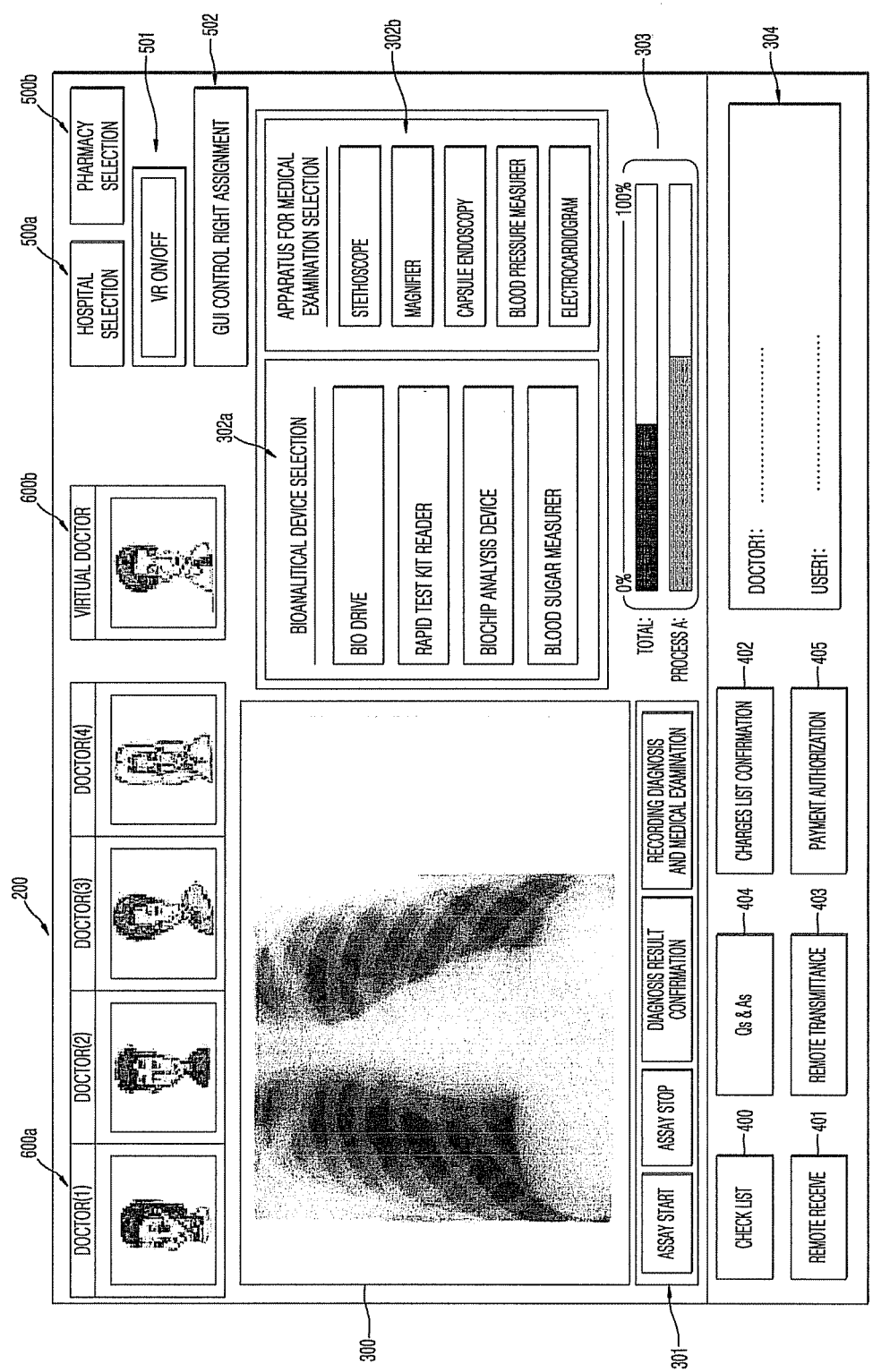
FIG. 11 shows the GUI of a remote medical-diagnosis system in which the medical expert transmits a chest X-ray taken when the user visited the hospital to the user's terminal, displays the chest X-ray on the medical service window, and explains the chest X-ray to the user in a remote area.

FIG. 11 shows the GUI 200 of a remote medical-diagnosis system in which the medical expert transmits a chest X-ray taken when the user visited the hospital to the user's terminal, displays the chest X-ray on the medical service window, and explains the chest X-ray to the user in a remote area.

Figure 12:
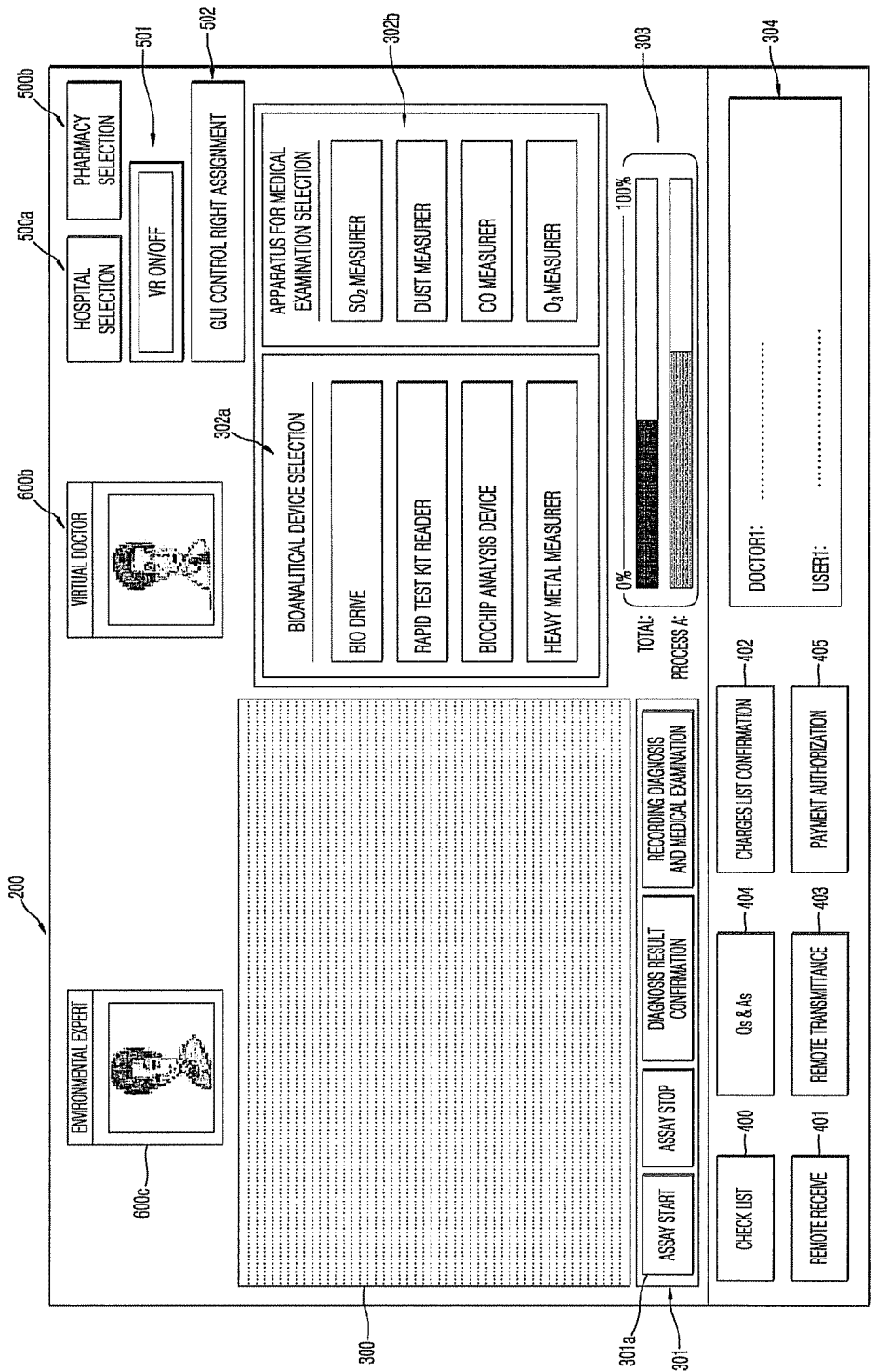
FIG. 12 shows the GUI of a remote medical-diagnosis system, which provides a remote diagnosis service using the bioanalytical device for detecting environmental pollution and the apparatus for medical examination.

FIG. 12 shows the GUI 200 of a remote medical-diagnosis system, which provides a remote diagnosis service using the bioanalytical device 100 for detecting environmental pollution and the apparatus 101 for medical examination. In this regard, an environmental expert 600c, instead of the medical expert, performs a remote diagnosis service.

Figure 13:
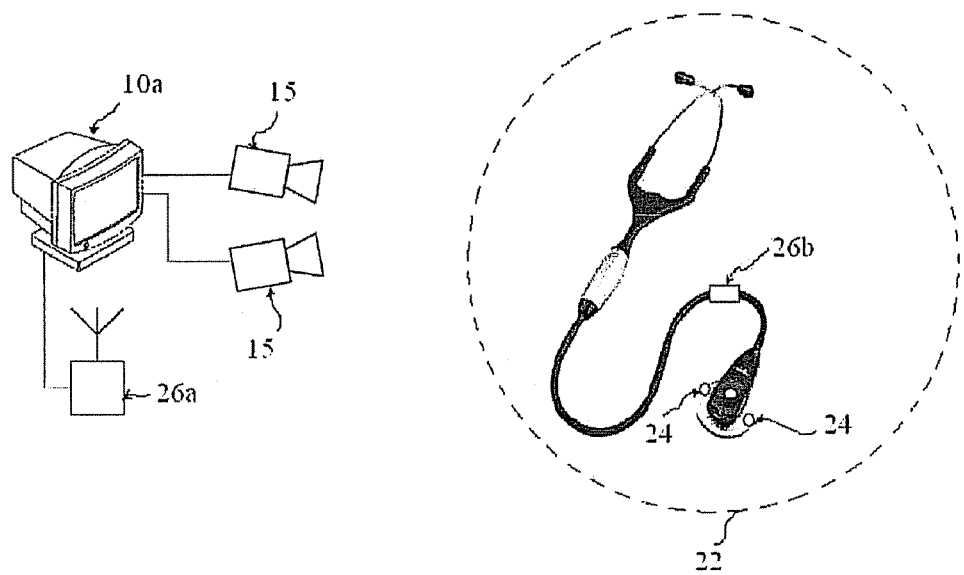
FIG. 13 shows a stethoscope to which a marker is attached, thereby facilitating a video tracking, a motion tracking, a capture and a standard coordinate set up, and a recognition of the apparatus for medical examination using a camera.

FIG. 13 shows a stethoscope 22 to which a marker 24 is attached, thereby facilitating a video tracking, a motion tracking, a capture and standard coordinate set up, and a recognition of the apparatus 101 for medical examination using the camera 15.

The position and orientation of the apparatus 101 for medical examination may be three-dimensionally identified using the marker 24, and the state of the user using the apparatus 101 for medical examination may be tracked or monitored in real time by cumulatively tracking the position of the marker 24.

The apparatus 101 for medical practice and the bioanalytical device 100 may be connected to the user's terminal 10a in wired or wireless manner.

The stethoscope 22 also includes a radio transmit/receive device 26a transmitting a command for controlling on/off or operation of the marker 24 (e.g., a LED) of the stethoscope 22 or receiving signals obtained from the stethoscope 22. The stethoscope 22 also includes a radio transmit/receive device 26b receiving a command from the user's terminal 10a or transmitting signals obtained from the stethoscope 22.

Figure 14:
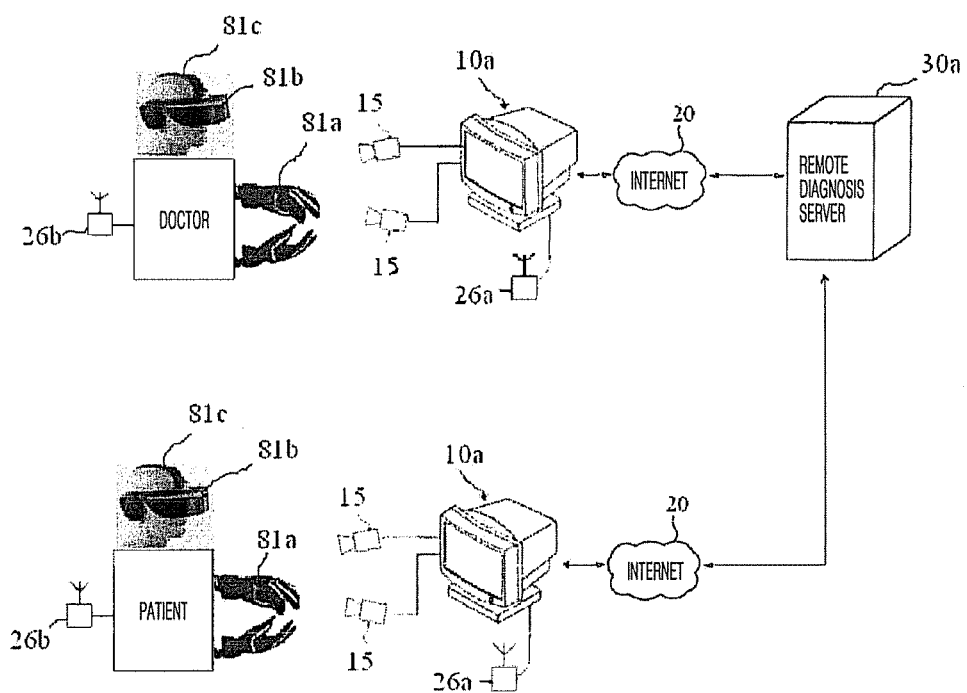
FIG. 14 shows the remote medical-diagnosis system employing virtual reality tools according to an embodiment of the present invention.

FIG. 14 shows the remote medical-diagnosis system employing virtual reality tools according to an embodiment of the present invention. The user or the user and the medical expert may use the virtual reality tools.

The user's terminal 10a and the medical expert's terminal 10b may further include virtual reality tools such as a pair of VR glasses, a VR cap, VR gloves, etc., in order to be interfaced with the virtual doctor.

Industrial Applicability

According to the remote medical-diagnosis system and the method of operating the remote medical-diagnosis system according to the present invention, most types of medical examinations such as a blood examination of a patient can be conducted without visiting a hospital, and instructions as how to use an apparatus for medical examination are automatically provided to the patient.

In addition, the patient can receive an automatic diagnostic service from a virtual doctor as well as a real doctor if required, choose the virtual doctor or the real doctor to get a diagnostic service, and also select one of the real doctors and pharmacists.

In addition, a personalized diagnosis can be obtained since the diagnosis results and the patient's constitution are shared by not only the hospital but also the pharmacy, and the processes for signing up and authentication are simplified.

The invention claimed is:

1. A remote medical-diagnosis system comprising:
a bio-disc or a biochip performing biological, chemical or biochemical reactions with a sample, and having a barcode or a radio frequency integrated circuit (RF IC);
a bioanalytical device comprising: a first authentication unit analyzing results of reactions performed by the bio-disc or the biochip and including a reader reading the barcode or the RF IC to authenticate a product ID of the bio-disc or the biochip, and a recording unit recording measured data corresponding to the results to the RF IC;
a user's terminal comprising a transmitter transmitting the measured data and the product ID of the bioanalytical device to a remote diagnosis server via a communication network, and a first consulting service unit providing a consulting service from a medical expert;
a virtual doctor residing as a software on the user's terminal, the virtual doctor comprising a guideline unit to provide a user with guidelines and instructions as how to use the bioanalytical device, and a diagnosis unit self-analyzing the measured data using mathematical calculations and outputting results of a diagnosis;
a medical expert's terminal comprising a receiver receiving the measured data via the communication network, and a second consulting service unit providing the user with a consulting service; and
a remote diagnosis server comprising a second authentication unit authenticating a product ID of the bioanalytical device, an ID registration unit registering and storing the product ID of the bioanalytical device authenticated by the second authentication unit, an expert selecting unit connecting the user with the medical expert during periodic medical consultations and connecting the user with the virtual doctor except during the periodic medical consultations, a connection blocking unit blocking a connection between the user and the virtual doctor when a periodic medical consultation term has elapsed, and a priority connection unit connecting the user with the medical expert upon receiving a signal requesting for a priority connection even during non-periodic medical consultations, wherein the user's terminal or the remote diagnosis server further comprises a monitoring unit which monitors processes of sampling blood and injecting the sample into the bioanalytical device in real time, or monitors the status of serum separation of the blood injected into the bio-disc or bio-chip, and wherein serum separation is monitored including:

determining whether serum separation is normally performed by monitoring the state of serum centrifuged or separated using a serum separation device; and sending a warning message to the user or recording the abnormal serum separation in a history management list if the serum separation is not normally performed.

2. The remote medical-diagnosis system of claim 1, wherein the recording unit saves the product ID of the corresponding bioanalytical device used for obtaining the measured data into the RF IC, saves a cumulative history of a past diagnosis results made by the virtual doctor or the medical expert as received from the remote diagnosis server into the RF IC, saves the diagnosis results obtained from the virtual doctor or the medical expert and the corresponding ID of the medical expert into the RF IC, or stores an ID and a password of the user, which are essential for signing up and authentication of the remote diagnosis server, in the RF IC.

3. The remote medical-diagnosis system of claim 1, wherein the signal requesting for a priority connection is a signal requested by the user, a signal indicating abnormal conditions based on the data obtained by the virtual doctor, or a signal representing an excess of the number limit on the consulting services by the virtual doctor.

4. The remote medical-diagnosis system of claim 1, wherein the user's terminal further comprises a display which displays the status of operation and progress of the bioanalytical device in real time, displays a rate of progress of the bioanalytical device, or displays the measured data in terms of numbers, in a graph, or a high-medium-low form.

5. The remote medical-diagnosis system of claim 1, wherein the user's terminal comprises a control assignment button in order to assign a remote control right to the medical expert.

6. The remote medical-diagnosis system of claim 1, further comprising at least one apparatus for medical examination connected to the user's terminal.

7. The remote medical-diagnosis system of claim 1, further comprising an assay stop process unit which requests an ID and a password of the user upon a request for stopping an assay by the user while performing an assay of the sample using the bio-disc or the biochip, records a historical fact of the assay stop to the RF IC if the assay is stopped since the ID and password of the user match the stored value, or transmits the historical fact of the assay stop to the remote diagnosis server.

8. The remote medical-diagnosis system of claim 1, wherein the medical expert's terminal further comprises a prescription generating unit which generates a medical prescription by the medical expert, and the remote diagnosis server further comprises a medicine preparation request unit which receives the prescription and requests a pharmacist to prepare medicine according to the prescription and transmit the medicine, and a payment unit by which the user pays fees for the preparation and transmission of the medicine with electronic money or a card.

9. The remote medical-diagnosis system of claim 1, wherein the user's terminal or the remote diagnosis server further comprises an automatic notifying device which notifies the user with information on a medical examination schedule, a hospital visit schedule, or a medicine intake schedule.

10. The remote medical-diagnosis system of claim 1, wherein the user's terminal further comprises a validity checking unit which notifies the user of invalid use of the bio-disc or the biochip when the validity period is over, or stores the invalid use in the RF IC as a history management list or transmits the invalid use to the remote diagnosis server.

11. The remote medical-diagnosis system of claim 1, wherein the user's terminal further comprises a humidity checking unit which notifies the user of excess humidity by sending a warning message when the bio-disc or the biochip is exposed to excess humidity, or stores the excess humidity in the RF IC as a history management list or transmits the excess humidity to the remote diagnosis server.

12. The remote medical-diagnosis system of claim 1, wherein the user's terminal further comprises a RF IC reader which provides the user with information, read from the RF IC, selected from the group consisting of the types, a version, a date of manufacture, a validity period, and a diagnosable disease list of the bio-disc or the biochip loaded on the bioanalytical device, user precautions, details of a history management list, medical data, and next examination date after an authentication of a password by matching a password stored in the RF IC.

13. The remote medical-diagnosis system of claim 1, wherein the user's terminal further comprises an information access unit which transmits a product ID read from the RF IC of the bio-disc or the biochip loaded on the bioanalytical device to the remote diagnosis server, and provides the user with information, received from the remote diagnosis server, selected from the group consisting of the types, a version, a date of manufacture, a validity period, and a diagnosable disease list of the products corresponding to the product ID, user precautions, details of a history management list, medical data, and next examination date, after an authentication of a password by matching a password stored in the remote diagnosis server.

14. The remote medical-diagnosis system of claim 1, wherein the bioanalytical device further comprises a sanitation grade display unit which tests food-born pathogens in food establishments or restaurants and transmits test data corresponding to the food-born pathogens to the remote diagnosis server, and displays a sanitation level of food graded by the environmental expert connected to the remote diagnosis server or food poisoning analysis software residing on the remote diagnosis server, based on the test data.

15. The remote medical-diagnosis system of claim 1, wherein the bioanalytical device further comprises a positional information receiver which receives positional information using a global positioning system (GPS) by connecting the bioanalytical device with a cellular phone.

16. The remote medical-diagnosis system of claim 1, wherein the measured data is read and the product ID of the bioanalytical device from the RF IC when a used bio-disc or a used biochip is loaded on the bioanalytical device;

the measured data is transmitted and the product ID of the bioanalytical device to the remote diagnosis server; and the measured data is regarded as invalid if the product ID of the bioanalytical device used to obtain the measured data is not registered in the remote diagnosis server.

17. The remote medical-diagnosis system of claim 1, further comprising providing the medical expert with a cumulation of the medical data made by the virtual doctor before the periodic medical consultations during the periodic medical consultations.

18. The remote medical-diagnosis system of claim 1, further comprising providing the user with guidelines and instructions from the virtual doctor or medical expert about sampling blood and injection of the blood into the bioanalytical device in real time.

19. The remote medical-diagnosis system of claim 1, further comprising monitoring operation and progress of the bioanalytical device in real time, displaying a rate of progress of the bioanalytical device, and displaying the measured data in terms of numbers, in a graph, or a high-medium-low form.

20. The remote medical-diagnosis system of claim 1, further comprising:

generating a prescription by the medical expert;

receiving the prescription and requesting medicine preparation according to the prescription and transmittance of the medicine; and paying fees for the preparation and transmittance of the medicine using electronic money or a card.

21. The remote medical-diagnosis system of claim 1, further comprising authenticating the user by identifying information on the user's health insurance.

22. The remote medical-diagnosis system of claim 1, further comprising notifying the user with information on a medical examination schedule, a hospital visit schedule, or a medicine intake schedule.

* * * * *

UNITED STATES PATENT AND TRADEMARK OFFICE
CERTIFICATE OF CORRECTION

| | | |
|---|---|---|
| PATENT NO. | : 8,630,867 B2 | Page 1 of 1 |
| APPLICATION NO. | : 12/596373 | |
| DATED | : January 14, 2014 | |
| INVENTOR(S) | : Jae-chern Yoo | |

It is certified that error appears in the above-identified patent and that said Letters Patent is hereby corrected as shown below:

On the Title Page

Column 1, Item [54] (Title), lines 1-2, delete "SYSTEM METHOD" and insert -- SYSTEM AND METHOD --.

Column 2, Item [57] (Abstract), lines 13-14, delete "outputing" and insert -- outputting --, therefore.

In the Specification

Column 1, in the title, lines 1-2, delete "SYSTEM METHOD" and insert -- SYSTEM AND METHOD --.
Column 1, in the Cross Reference to Related Applications, line 2, delete "Apr. 11, 2008," and insert -- Apr. 22, 2008, --.
Column 1, in the Cross Reference to Related Applications, line 4, delete "Apr. 12, 2007," and insert -- Apr. 23, 2007, --.

In the Claims

Column 31, line 13, in claim 1, delete "bio-chip," and insert -- biochip --, therefore.

Signed and Sealed this
Twentieth Day of October, 2015

Michelle K. Lee
*Director of the United States Patent and Trademark Office*